(12) United States Patent
Takahashi et al.

(10) Patent No.: US 10,392,652 B2
(45) Date of Patent: Aug. 27, 2019

(54) MICRO RNA DETECTION METHOD USING TWO PRIMERS TO PRODUCE AN AMPLIFIED DOUBLE STRANDED DNA FRAGMENT HAVING A SINGLE STRANDED REGION AT ONE END

(71) Applicant: KANEKA CORPORATION, Osaka (JP)

(72) Inventors: Koji Takahashi, Takasago (JP); Shigehiko Miyamoto, Takasago (JP); Sotaro Sano, Takasago (JP); Jun Tomono, Takasago (JP)

(73) Assignee: KANEKA CORPORATION, Osaka (JP)

( * ) Notice: Subject to any disclaimer, the term of this patent is extended or adjusted under 35 U.S.C. 154(b) by 357 days.

(21) Appl. No.: 15/037,920

(22) PCT Filed: Nov. 21, 2014

(86) PCT No.: PCT/JP2014/080854
§ 371 (c)(1),
(2) Date: May 19, 2016

(87) PCT Pub. No.: WO2015/076356
PCT Pub. Date: May 28, 2015

(65) Prior Publication Data
US 2016/0362732 A1    Dec. 15, 2016

(30) Foreign Application Priority Data

Nov. 22, 2013 (JP) .................................. 2013-241938

(51) Int. Cl.
*C12P 19/34* (2006.01)
*C12Q 1/6834* (2018.01)
*C12Q 1/6816* (2018.01)

(52) U.S. Cl.
CPC ......... *C12Q 1/6834* (2013.01); *C12Q 1/6816* (2013.01)

(58) Field of Classification Search
None
See application file for complete search history.

(56) References Cited

U.S. PATENT DOCUMENTS 5,310,650 A    5/1994  McMahon et al.
5,403,711 A    4/1995  Walder et al.
(Continued)

FOREIGN PATENT DOCUMENTS

CN    1459506 A    12/2003
CN    1697883 A    11/2005
(Continued)

OTHER PUBLICATIONS

Bandyopadhyay et al., "Development of the human cancer microRNA network," Silence (2010), vol. 1, No. 6, pp. 1-14.
(Continued)

*Primary Examiner* — Kenneth R Horlick
(74) *Attorney, Agent, or Firm* — Birch, Stewart, Kolasch & Birch, LLP

(57) ABSTRACT

Provided is a method for detecting small RNAs in a simple and highly accurate manner. Provided is a nucleic acid detection method including the following steps (a) to (c): (a) carrying out a reverse transcription reaction using a target RNA as a template and a reverse transcription primer having on its 5'-end side a sequence non-complementary to the target RNA to produce a reverse transcription product longer than the target RNA; (b) carrying out a nucleic acid amplification reaction using the reverse transcription product as a template and two primers to produce an amplified double-stranded DNA fragment having a single-stranded region at least at one end; and (c) hybridizing the single-stranded
(Continued)

region of the amplified double-stranded DNA fragment to an oligonucleotide probe immobilized on a solid phase.

29 Claims, 8 Drawing Sheets

Specification includes a Sequence Listing.

(56) References Cited

U.S. PATENT DOCUMENTS

| | | | |
|---|---|---|---|
| 5,475,098 | A | 12/1995 | Hall et al. |
| 5,525,494 | A | 6/1996 | Newton |
| 5,629,158 | A | 5/1997 | Uhlen |
| 5,874,216 | A | 2/1999 | Mapes |
| 5,925,518 | A | 7/1999 | Earle et al. |
| 5,939,292 | A | 8/1999 | Gelfand et al. |
| 7,932,060 | B2 | 4/2011 | Nadeau et al. |
| 9,783,844 | B2 * | 10/2017 | Takahashi ............ C12Q 1/6834 |
| 9,920,356 | B2 * | 3/2018 | Takahashi ............ C12Q 1/6834 |
| 2003/0108913 | A1 | 6/2003 | Schouten |
| 2005/0142559 | A1 | 6/2005 | Makrigiorgos |
| 2006/0134802 | A1 | 6/2006 | Donati et al. |
| 2008/0274464 | A1 | 11/2008 | Goto et al. |
| 2009/0047673 | A1 | 2/2009 | Cary |
| 2009/0136956 | A1 | 5/2009 | Merante et al. |
| 2010/0291666 | A1 | 11/2010 | Collier et al. |
| 2010/0330564 | A1 | 12/2010 | Tomono |
| 2010/0330574 | A1 | 12/2010 | Whitman et al. |
| 2011/0244597 | A1 | 10/2011 | Tsukada et al. |
| 2012/0053063 | A1 | 3/2012 | Rigatti et al. |
| 2013/0052652 | A1 | 2/2013 | Schneider et al. |
| 2014/0065725 | A1 | 3/2014 | Takahashi et al. |
| 2014/0206567 | A1 | 7/2014 | Niwa et al. |
| 2015/0203905 | A1 | 7/2015 | Takahashi et al. |

FOREIGN PATENT DOCUMENTS

| | | |
|---|---|---|
| CN | 1891832 A | 1/2007 |
| CN | 1982325 A | 6/2007 |
| CN | 101137759 A | 3/2008 |
| CN | 101845511 A | 9/2010 |
| EP | 0416817 A2 | 3/1991 |
| EP | 1634962 A1 | 3/2006 |
| EP | 2208795 A1 | 7/2010 |
| EP | 2 410 063 A1 | 1/2012 |
| EP | 2 762 562 A1 | 8/2014 |
| EP | 2789689 A1 | 10/2014 |
| JP | 64-63865 A | 3/1989 |
| JP | 2-283299 A | 11/1990 |
| JP | 3-272686 A | 12/1991 |
| JP | 5-252998 A | 10/1993 |
| JP | 7-75599 A | 3/1995 |
| JP | 2001-157598 A | 6/2001 |
| JP | 2002-530677 A | 9/2002 |
| JP | 2002-534434 A | 10/2002 |
| JP | 2003-504018 A | 2/2003 |
| JP | 2004-502464 A | 1/2004 |
| JP | 2006-201062 A | 8/2006 |
| JP | 2006-524993 A | 11/2006 |
| JP | 2007-111048 A | 5/2007 |
| JP | 2007-526443 A | 9/2007 |
| JP | 2008-525037 A | 7/2008 |
| JP | 2009-521924 A | 6/2009 |
| JP | 2009-162535 A | 7/2009 |
| JP | 2009-529058 A | 8/2009 |
| JP | 2009-296948 A | 12/2009 |
| JP | 2010-14507 A | 1/2010 |
| JP | 2010-513854 A | 4/2010 |
| JP | 2010-516284 A | 5/2010 |
| JP | 2010-533494 A | 10/2010 |
| JP | 4879975 B2 | 2/2012 |
| JP | 2013-530698 A | 8/2013 |
| WO | WO 94/24563 A1 | 10/1994 |
| WO | WO 96/36733 A1 | 11/1996 |
| WO | WO 98/14610 A2 | 4/1998 |
| WO | WO 00/31539 A1 | 6/2000 |
| WO | WO 00/47767 A1 | 8/2000 |
| WO | WO 01/21637 A1 | 3/2001 |
| WO | WO 02/04668 A2 | 1/2002 |
| WO | WO 02/24944 A2 | 3/2002 |
| WO | WO 00/40592 A1 | 7/2002 |
| WO | WO 2004/099438 A1 | 11/2004 |
| WO | WO 2004/109285 A1 | 12/2004 |
| WO | WO 2006/043387 A1 | 4/2006 |
| WO | WO 2006/071770 A2 | 7/2006 |
| WO | WO 2006/095550 A1 | 9/2006 |
| WO | WO 2007/103549 A2 | 9/2007 |
| WO | WO 2008/075213 A2 | 6/2008 |
| WO | WO 2008/092016 A2 | 7/2008 |
| WO | WO 2009/012246 A2 | 1/2009 |
| WO | WO 2009/034842 A1 | 3/2009 |
| WO | WO 2010/061772 A1 | 6/2010 |
| WO | WO 2010-106997 A1 | 9/2010 |
| WO | WO 01/02559 A1 | 1/2011 |
| WO | WO 2011/137911 A2 | 11/2011 |
| WO | WO 2011/159256 A1 | 12/2011 |
| WO | WO 2012/070618 A1 | 5/2012 |
| WO | WO 2013/038534 A1 | 3/2013 |
| WO | WO 2013/039228 A1 | 3/2013 |
| WO | WO 2013/040491 A2 | 3/2013 |
| WO | WO 2013/162026 A1 | 10/2013 |

OTHER PUBLICATIONS

Chen et al., "Real-time Quantification of microRNAs by stem-loop RT-PCR," Nucleic Acids Research (2005), vol. 33, No. 20, e179, pp. 1-9.

English translation of International Preliminary Report on Patentability and Written Opinion dated Jun. 2, 2016, in PCT International Application No. PCT/JP2014/080854.

Jung et al., "Fabriction of single-walled carbon nanotubes dotted with Au nanocrystals: Potential DNA delivery nanocarriers," Carbon (2010), vol. 48, pp. 1070-1078.

Liang et al., "Construction of a photo-switchable gene for turning on and off gene expression with light irradiation," Nucleic Acids Symposium Series No. 52 (Sep. 8, 2008), pp. 19-20.

Liang et al., "Nick Sealing by T4 DNA Ligase on a Modified DNA Template: Tethering a Functional Molecule on D-Threoninol," Chem. Eur. J. (2011), vol. 17, pp. 10388-10396.

Sasaki, T., Easy Detection of Multiple Genes, Highlighting Japan (Mar. 2013), pp. 24-25.

Sharbati-Tehrani et al., "miR-Q: A novel quantitative RT-PCR approach for the expression profiling of small RNA molecules such as miRNAs in a complex sample," BMC Molecular Biology (2008), vol. 9, No. 34, pp. 1-13.

Asanuma et al., "Photo-Responsive Oligonucleotides Carrying Azobenzene in the Side-Chains," Tetrahedron Letters, vol. 39, No. 49, 1998, pp. 9015-9018.

Bindon et al., "Biologically-generated primer for PCR: PCR primer of unknown sequence," Nucleic Acid Research, vol. 26, No. 13, 1998, pp. 3305-3308.

Brownie et al., "The elimination of primer-dimer accumulation in PCR," Nucleic Acids Research, vol. 25, No. 16, 1997, pp. 3235-3241.

Carter et al., "Lateral flow microarrays: a novel platform for rapid nucleic acid detection based on miniaturized lateral flow chromatography," Nucleic Acids Research, vol. 35, No. 10, e74, 2007 (Published online May 3, 2007), pp. 1-11.

Corstjens et al., "Lateral-flow and up-converting phosphor reporters to detect single-stranded nucleic acids in a sandwich-hybridization assay," Analytical Biochemistry, vol. 312, 2003, pp. 191-200.

Hauser et al., "Utilising the left-helical conformation of L-DNA for analysing different marker types on a single universal microarray platform," Nucleic Acids Research, vol. 34, No. 18, 2006 (published online Sep. 20, 2006), pp. 5101-5111.

Hayashi et al., "Application of L-DNA as a molecular tag," Nucleic Acids Symposium Series, No. 49, 2005, pp. 261-262.

International Preliminary Report on Patentability and English translation of the Written Opinion of the International Searching Author-

(56) References Cited

OTHER PUBLICATIONS ity (Forms PCT/IB/373 and PCT/ISA/237) for International Application No. PCT/JP2011/077050, dated Jun. 12, 2013.
International Preliminary Report on Patentability and English translation of the Written Opinion of the International Searching Authority (Forms PCT/IB/373 and PCT/ISA/237) for International Application No. PCT/JP2013/062488, dated Oct. 28, 2014.
Jesus De La Calle et al., "Evaluation of two real-time PCR methods to direct detection of groupB streptococci against conventional . . . ," 19th European Congress of Clinical Microbiology and Infectious Diseases, Helsinki, Finland, May 16-19, 2009, 1 page (Abstract No. P1842 provided only).
Kaluz et al., "Ligation-independent cloning of PCR products with primers containing nonbase residues," Nucleic Acids Research, vol. 22, No. 22, 1994, p. 4845.
Liu et al., "A universal biosensor for multiplex DNA detection based on hairpin probe assisted cascade signal amplification," Chem. Comm., vol. 49, 2013, pp. 5165-5167.
Newton et al., "The production of PCR products with 5' single-stranded tails using primers that incorporate novel phosphoramidite intermediates," Nucleic Acids Research, vol. 21, No. 5, 1993, pp. 1155-1162.
Oku et al., "Development of oligonucleotide lateral-flow immunoassay for multi-parameter detection," Journal of Immunological Methods, vol. 258, 2001, pp. 73-84.
Preceedings of the 77th Annual Meeting of the Chemical Society of Japan, Union of Chemistry-Related Societies Research Workshop, Sep. 10, 1999, p. 229.
Reinhartz et al., "A novel rapid hybridization technique: paper chromatography hybridization assay (PACHA)," Gene, vol. 136, 1993, pp. 221-226.
SA Scientific, "Dipstick 'Eiken' ADENO," 341464-E, Aug. 2009, pp. 1-2.
SA Scientific, "Dipstick 'Eiken' ROTA," 341463-E, Aug. 2009, pp. 1-2.
Shimizu et al., "Evaluation of Immunochromatography Based Rapid Detection Kit of Rotavirus and Adenovirus," Journal of the Japanese Association for Infectious Diseases, vol. 75, No. 12, Dec. 20, 2001, pp. 1040-1046, with English abstract.
Ujiiye, "Useful method "Nucleic Acid-Chromatography" for genetic testing," Clinical Chemistry, vol. 36, No. 1, Jan. 2007, pp. 19-24 (7 pages total), with partial English translation.
Vircell Microbiologists, "Speed-oligo Quick Visual Oligochromatography, Innovation design, smart combination . . . all the advantages of Molecular Biology in a quick detection," Informative Dossier, Second Edition, Jun. 2010, 20 pages.
Wada et al., "Functionalization of PNA—Novel Strategy for Active Control of DNA Recognition by External Factors using Peptide Ribonucleic Acids (PRNA)," Journal of Synthetic Organic Chemistry, vol. 63, No. 1, 2005, pp. 63-75, with English abstract.
Wada, "Separate Analysis of Complementary Strands of Restriction Enzyme-digested DNA. An Application of Restriction Fragment Mass Mapping by Matrix-assisted Laser Desorption/Ionization Mass Spectrometry," Journal of Mass Spectrometry, vol. 33, 1998, pp. 187-192 (7 pages total).
Yamazawa et al., "Photo-Regulation of DNA Polymerase Reaction by Oligonucleotides Bearing an Azobenzene," Supporting Information, Angew. Chem., 2000, 5 pages.
Yamazawa et al., "Photoregulation of the DNA Polymerase Reaction by Oligonucleotides Bearing an Azobenzene," Angew. Chem. Int. Ed., vol. 39, No. 13, 2000, pp. 2356-2357.

\* cited by examiner

MICRO RNA DETECTION METHOD USING TWO PRIMERS TO PRODUCE AN AMPLIFIED DOUBLE STRANDED DNA FRAGMENT HAVING A SINGLE STRANDED REGION AT ONE END

TECHNICAL FIELD

The present invention relates to a simple method for detecting small RNAs.

REFERENCE TO SEQUENCE LISTING SUBMITTED VIA EFS-WEB

This application includes an electronically submitted sequence listing in .txt format. The .txt file contains a sequence listing entitled "2016-08-26 5051-0405PUS1_ST25.txt" created on Aug. 26, 2016 and is 14,416 bytes in size. The sequence listing contained in this .txt file is part of the specification and is hereby incorporated by reference herein in its entirety.

BACKGROUND ART

Various types of RNAs are expressed in vivo. In addition to mRNAs encoding amino acid sequences of proteins, a large amount of RNAs encoding non-translatable regions, known as non-coding RNAs, are found. Among non-coding RNAs, micro RNAs (miRNAs) are small RNAs of 18 to 25 nucleotides present in cells. Micro RNAs play important regulatory roles in development of animals, plants, and viruses. Further, recent studies have revealed that miRNAs have regulatory functions in translation of proteins in animal cells. Studies on miRNAs have dramatically advanced since then, and 24,521 miRNAs are now registered in the miRBase database version 19 (http://www.mirbase.org/), and 25,646 articles related to miRNAs are included in the PubMed database (http://www.ncbi.nlm.nih.gov/pubmed). These reflect the high level of interest in miRNAs and the importance of miRNAs.

Micro RNAs regulate and inhibit translation by binding to target messenger RNAs. Presumably, miRNAs regulate transcription and expression of about 30% of the human genome.

Moreover, regarding the importance of miRNAs, it has been demonstrated that miRNAs are involved in development, growth, proliferation, apoptosis, differentiation, and various cellular expression processes, including various human diseases such as cancer and diabetes.

Non-Patent Literature 1 emphasizes the significance of miRNAs in cancer and describes involvement of miRNAs in various types of human cancer. Non-Patent Literature 1 states that measuring changes in the expression level of miRNAs is greatly useful for advancing cancer research.

Conventional methods for detecting miRNAs include qRT-PCR and microarray assay. However, since miRNAs are small RNAs each consisting of 18 to 25 nucleotides, they have been very difficult to amplify or detect. Non-Patent Literature 2, Patent Literature 1, and Non-Patent Literature 3 have suggested solutions to this problem. Non-Patent Literature 2 discloses a qRT-PCR assay including a gene-specific reverse transcription step and a subsequent fluorescent detection step using a gene-specific forward primer with TaqMan probe and a universal reverse primer. Also in Patent Literature 1, miRNAs are detected by fluorescence using similar reverse transcription reaction primers. Non-Patent Literature 3 discloses a qRT-PCR assay including a gene-specific reverse transcription step and a subsequent SYBR (registered trademark) green qPCR step using a gene-specific forward primer and two universal primers.

However, there is no known method for detecting miRNAs by qRT-PCR or carrying out microarray assay in a rapid and simple manner.

CITATION LIST

Patent Literature

Patent Literature 1: Japanese Patent No. 4879975

Non Patent Literature

Non Patent Literature 1: Bandyopadhyay et al. Silence 2010, 1:6
Non Patent Literature 2: Chen C et al. Nucleic Acids Res. 2005 Nov. 27; 33 (20): e179.
Non Patent Literature 3: Sharbati-Tehrani et al. BMC Molecular. 2008, 9:34

SUMMARY OF INVENTION

Technical Problem

In genetic diagnosis and genetic testing in clinical practice, inconvenience and burden are often placed on patients in terms of testing costs and several hospital visits because such diagnosis and testing require large-scale, expensive test devices and time for testing. In this context, due to the need to reduce the burden on patients and testers while maintaining the accuracy of testing, there is a demand for simple, rapid, highly specific methods or low-cost methods that do not require any special equipment. The present invention was made to solve the above problems. An object of the present invention is to provide a nucleic acid detection method which extends the length of a small RNA by a reverse transcription reaction to allow for an efficient PCR reaction, and further produces a PCR product having a single-stranded region to take advantage of the high specificity of hybridization techniques and reduce the time length and the number of steps required for detection of PCR products, thereby allowing for visual detection in a simple and highly accurate manner without the need for special equipment, as well as a nucleic acid detection device or kit.

Solution to Problem

The present inventors conducted extensive studies to solve the above problems and independently found the following. Specifically, a target RNA is reverse transcribed using a reverse transcription primer to produce a cDNA longer than the target RNA; the cDNA is efficiently amplified to obtain a double-stranded nucleic acid having a single-stranded region; and the amplified nucleic acid fragment is bound to a solid phase containing an oligonucleotide probe capable of hybridizing to the single-stranded region, followed by detection. Such a method allows for detection of the amplified nucleic acid fragment in a simple and highly accurate manner without the need for special equipment. The present invention was thus completed.

The present invention relates to a nucleic acid detection method, including the following steps (a) to (c):
(a) carrying out a reverse transcription reaction using a target RNA as a template and a reverse transcription primer having on its 5'-end side a sequence non-complementary to the target RNA to produce a reverse transcription product longer than the target RNA;
(b) carrying out a nucleic acid amplification reaction using the reverse transcription product as a template and two primers to produce an amplified double-stranded DNA fragment having a single-stranded region at least at one end; and
(c) hybridizing the single-stranded region of the amplified double-stranded DNA fragment to an oligonucleotide probe immobilized on a solid phase.

Preferably, the target RNA has a base sequence of 10 or more bases.

Preferably, the target RNA has a base sequence of 15 or more bases.

Preferably, the target RNA is a micro RNA.

Preferably, the reverse transcription primer contains a sequence of three or more bases complementary to the target RNA.

Preferably, the method further includes before step (a) the step of adding a poly(A) sequence of three or more bases to the target RNA.

Preferably, the reverse transcription primer contains a poly(T) sequence of three or more bases.

Preferably, the reverse transcription primer contains on its 3'-end side a sequence of one or more bases complementary to the target RNA.

Preferably, the reverse transcription product is longer than the target RNA by three or more bases.

Preferably, the sequence non-complementary to the target RNA is a sequence containing therein mutually complementary sequences of five or more bases so as to be able to form a loop structure.

Preferably, the primer contains a tag region, a polymerase reaction inhibitory region, and a region having a sequence capable of hybridizing to the reverse transcription product or its complementary strand.

Preferably, the polymerase reaction inhibitory region contains a nucleic acid derivative.

Preferably, the nucleic acid derivative is at least one selected from the group consisting of an L-nucleic acid, a 3-deoxy-2-hydroxy-dN, a nucleic acid containing a modified base, a nucleic acid containing a damaged base, a nucleic acid containing a modified phosphate linkage, an RNA, a 2'-OMe-N, and derivatives thereof.

Preferably, the nucleic acid derivative is linked via a 5'-5' linkage to the region having a sequence capable of hybridizing to the reverse transcription product or its complementary strand and/or linked to the tag region via a 3'-3' linkage.

Preferably, the polymerase reaction inhibitory region contains a non-nucleic acid derivative.

Preferably, the non-nucleic acid derivative has a D-threoninol scaffold.

Preferably, the D-threoninol scaffold incorporates at least one selected from the group consisting of azobenzene, biotin, EDTA, and a chromophore.

Preferably, the non-nucleic acid derivative is at least one selected from the group consisting of a carbon chain ($C_n$), a PEG chain (($CH_2CH_2O)_n$), a disulfide-containing chain ($C_nSSC_n$), dithiol phosphoramidite, and derivatives thereof.

Preferably, the primer contains multiple types of polymerase reaction inhibitory regions and/or contains a plurality of polymerase reaction inhibitory regions.

Preferably, the tag region has a nucleic acid sequence in the same orientation as the region having a sequence capable of hybridizing to the reverse transcription product or its complementary strand.

Preferably, the tag region contains a nucleic acid sequence in the same orientation as the region having a sequence capable of hybridizing to the reverse transcription product or its complementary strand, and a nucleic acid sequence in the opposite direction.

Preferably, the amplified double-stranded DNA fragment is capable of binding to a labeling substance.

Preferably, the amplified double-stranded DNA fragment is capable of binding to a labeling substance via the single-stranded region.

Preferably, the amplified double-stranded DNA fragment is capable of binding to a labeling substance via a sequence containing a labeling substance-binding substance.

Preferably, the method further includes the step of binding the single-stranded region of the amplified double-stranded DNA fragment to a labeling substance.

Preferably, the labeling substance includes a colored carrier and allows for visual detection of the amplified double-stranded DNA fragment.

Preferably, the step of hybridizing the single-stranded region of the amplified double-stranded DNA fragment to an oligonucleotide probe immobilized on a solid phase is carried out on a nucleic acid detection device.

Preferably, the nucleic acid detection device is a chromatography device.

Preferably, the method includes the following steps (a) to (c):
(a) placing the amplified double-stranded DNA fragment in a zone on the nucleic acid detection device which is different from a zone where the oligonucleotide probe is immobilized,
(b) diffusing the amplified double-stranded DNA fragment on the device with a solvent toward the zone where the oligonucleotide probe is immobilized; and
(c) hybridizing the amplified double-stranded DNA fragment to the oligonucleotide probe in the zone where the oligonucleotide probe is immobilized.

Preferably, the method further includes before step (c) the step of binding the amplified double-stranded DNA fragment to the labeling substance.

Preferably, the method includes the following steps (d) to (h):
(d) placing the amplified double-stranded DNA fragment and the labeling substance in respective zones on the nucleic acid detection device which are different from the zone where the oligonucleotide probe is immobilized;
(e) diffusing the amplified double-stranded DNA fragment with a solvent toward the zone where the labeling substance is placed;
(f) binding the amplified double-stranded DNA fragment to the labeling substance in the zone where the labeling substance is placed;
(g) diffusing a complex formed by binding in step (f) on the device toward the zone where the oligonucleotide probe is placed; and
(h) hybridizing the complex to the oligonucleotide probe in the zone where the oligonucleotide probe is immobilized.

The present invention also relates to a nucleic acid detection device for use in the nucleic acid detection method, the nucleic acid detection device including a zone where the amplified double-stranded DNA fragment is placed; a chromatographic carrier carrying the oligonucleotide probe that binds to the amplified double-stranded DNA fragment; and an oligonucleotide probe labeled with a labeling substance.

Advantageous Effects of Invention

According to the present invention, a small RNA is reverse transcribed to extend the chain length so as to allow for an efficient DNA amplification reaction. Further, a single-stranded region of the resulting amplified DNA product can be used for specific binding to a solid phase, and the other side of the amplified DNA product can form a complex with a labeling compound. Thus, the amplified DNA product can be visually analyzed in a simple and rapid manner without the need for special equipment. Further, the detection of the structurally stable double-stranded DNA leads to higher detection sensitivity as compared to the detection of an entirely single-stranded DNA. In addition, two or more target nucleic acids in a sample can be simultaneously analyzed using multiple combinations of single-stranded regions of amplified products for binding to a solid phase and complementary oligonucleotide probes on the solid phase.

DESCRIPTION OF EMBODIMENTS

The present invention relates to a nucleic acid detection method including the following steps (a) to (c):
(a) carrying out a reverse transcription reaction using a target RNA as a template and a reverse transcription primer having on its 5'-end side a sequence non-complementary to the target RNA to produce a reverse transcription product longer than the target RNA;
(b) carrying out a nucleic acid amplification reaction using the reverse transcription product as a template and two primers to produce an amplified double-stranded DNA fragment having a single-stranded region at least at one end; and
(c) hybridizing the single-stranded region of the amplified double-stranded DNA fragment to an oligonucleotide probe immobilized on a solid phase.

The amplified double-stranded DNA fragment is obtained by carrying out a reverse transcription reaction of a target RNA in a sample as a template using a reverse transcription primer to produce a cDNA, and then carrying out a nucleic acid amplification reaction using a specific primer set.

The sample may be any sample that can be used as a template for a nucleic acid amplification reaction. Specific examples include any nucleic acids derived from biological samples, such as blood, biological fluids, tissues, oral mucosa, hair, nails, cultured cells, animals, plants, and microorganisms. Examples of RNAs that may be used include total RNA, messenger RNA, transfer RNA, ribosome RNA, antisense RNA, non-coding RNA, micro RNA (miRNA), pri-miRNA, pre-miRNA, small interfering RNA, small hairpin RNA, gRNA, snRNA, snoRNA, small temporal RNA, and Piwi-interacting RNA.

The RNA is not necessarily purified, and cells or tissues containing RNAs can be used directly in the reverse transcription and nucleic acid amplification reactions without being purified. The RNA preferably has a base sequence of 10 or more bases, more preferably a base sequence of 15 or more bases.

Moreover, a poly(A) sequence can be added to the 3' end of the target RNA before the reverse transcription reaction. The poly(A) (adenine) sequence to be added may have any length, but addition of 3 or more bases is preferred, and addition of 5 or more bases is more preferred.

Figure 1:
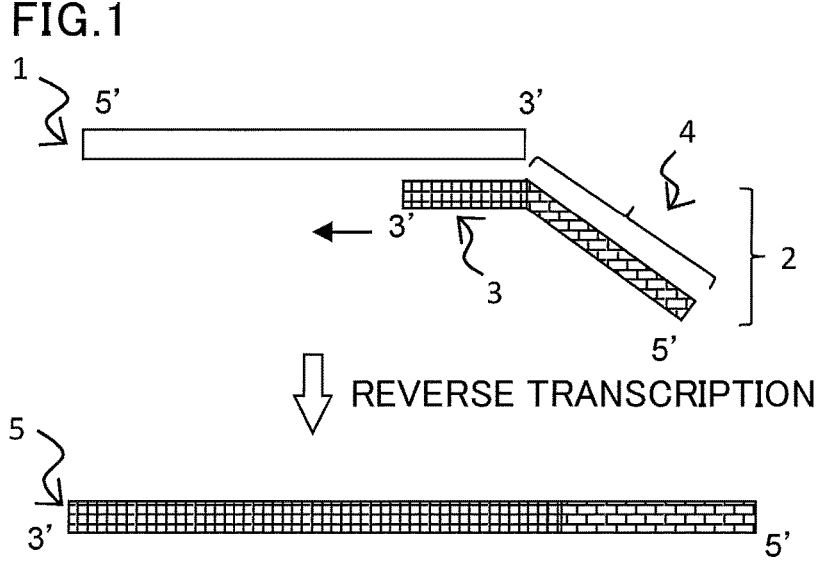
FIG. 1 is a conceptual diagram of a reverse transcription reaction using a reverse transcription primer having a sequence complementary to a target RNA and an additional sequence on the 5'-end side of the sequence.

The reverse transcription reaction is carried out using a reverse transcription primer having on its 5'-end side a sequence non-complementary to the target RNA. In the reverse transcription reaction, as shown in FIG. 1, the use of a reverse transcription primer 2 having a sequence 3 complementary to a portion of the sequence of a target RNA 1 and, further, any additional sequence 4 non-complementary to the target RNA on the 5'-end side of the sequence 3 allows for production of a reverse transcription product cDNA 5 containing an additional sequence not derived from the target RNA and having a length longer than the target RNA. The reverse transcription product is preferably longer than the target RNA by three or more bases.

Figure 2:
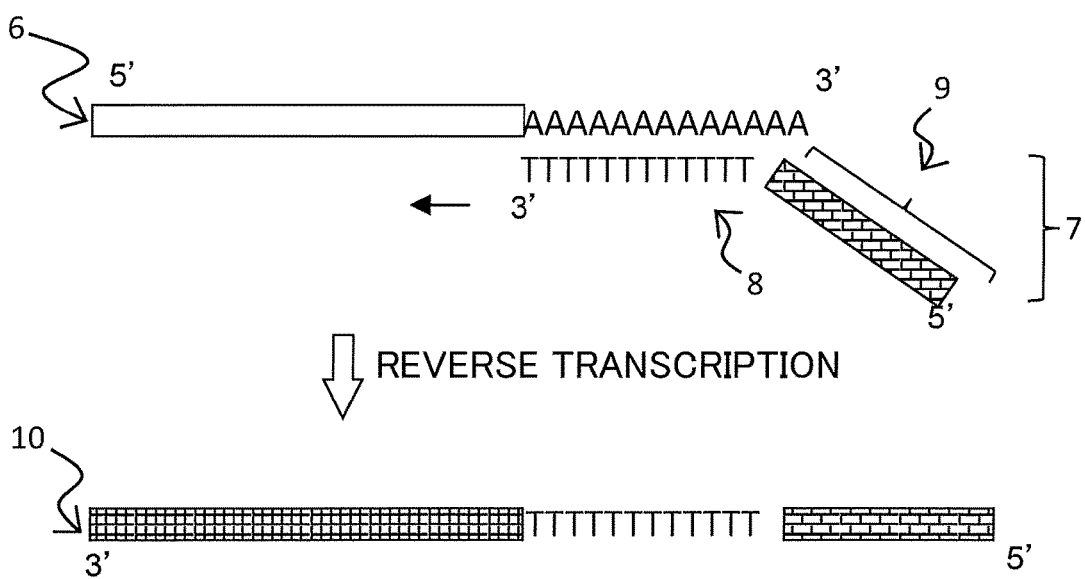
FIG. 2 is a conceptual diagram of a reverse transcription reaction of a target RNA to which a poly(A) sequence is added at the 3' end, using a reverse transcription primer having an additional sequence-poly(T)-VN (V=A, G, or C).

As another example of the reverse transcription reaction, as shown in FIG. 2, a target RNA 6 having a poly(A) sequence on the 3'-end side or a target RNA 6 to which a poly(A) sequence is added by a poly(A) polymerase can be reverse transcribed with a reverse transcription primer 7 having a poly(T) sequence 8 complementary to the poly(A) sequence and further having any additional sequence 9 non-complementary to the target RNA on the 5'-end side of the poly(T) sequence 8 to produce a reverse transcription product cDNA 10 containing an additional sequence non-complementary to the target RNA and having a length longer than the target RNA.

The number of target RNAs present may be one or two or more. The number of reverse transcription primers to be used in the reverse transcription reaction may be one or two or more.

The reverse transcription primer 2 contains a sequence complementary to the 3'-end side of the target RNA and also contains a tag sequence non-complementary to the target RNA. The reverse transcription primer 7 contains a sequence complementary to the 3'-end side of the target RNA or a poly(T) sequence complementary to the poly(A) sequence at the 3' end of the target RNA and also contains a tag sequence non-complementary to the target RNA. The poly(T) sequence preferably has a length of three or more bases. Also when the reverse transcription primer contains a poly(T) sequence, it preferably contains on its 3'-end side a sequence of one or more bases complementary to the target RNA.

The reverse transcription primer preferably contains a sequence (primer body region) of three or more bases complementary to the target RNA. The reverse transcription primer containing not more than two bases tends to be incapable of specific hybridization.

The sequence non-complementary to the target RNA in the reverse transcription primer is preferably a sequence containing therein mutually complementary sequences of five or more bases so as to be able to form a loop structure. When the reverse transcription primer forms a loop structure, the loop interferes with the binding to pri-miRNAs or pre-miRNAs and therefore their reverse transcription reactions cannot proceed easily. This allows for specific reverse transcription of a mature-miRNA.

Following the reverse transcription reaction, a nucleic acid amplification reaction is carried out using a specific primer set and the reverse transcription product produced as in FIG. 1 or FIG. 2.

The primer contains a tag region, a polymerase reaction inhibitory region, and a primer body region. The primer body region refers to a region having a sequence capable of hybridizing to the reverse transcription product or its complementary strand. The tag region and the polymerase reaction inhibitory region are not made double-stranded by the nucleic acid amplification reaction. For example, as described later, when the primer contains an L-nucleic acid, the L-nucleic acid serves both as a tag region and a polymerase reaction inhibitory region. Moreover, the primer may be a primer that contains a compound having a D-threoninol scaffold incorporating azobenzene, and an ordinary single-stranded DNA. In this case, the ordinary single-stranded DNA portion functions as a tag region, and the compound having a D-threoninol scaffold incorporating azobenzene functions as a polymerase reaction inhibitory region.

Figure 3:
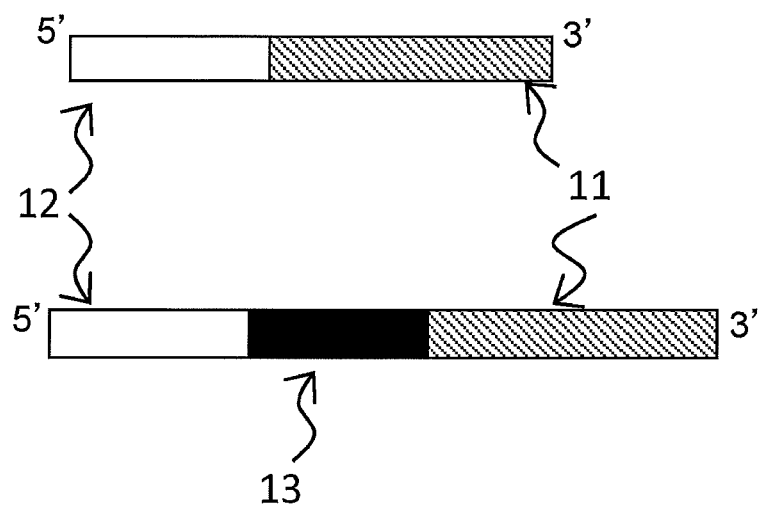
FIG. 3 is a conceptual diagram of a primer for PCR.

FIG. 3 shows a primer for amplifying a nucleic acid. This primer contains a tag region 12 on the 5'-end side of the primer which is not made double-stranded by the nucleic acid amplification reaction, and a primer body region 11. The primer may also have a polymerase reaction inhibitory region 13 between the primer body region and the tag region.

The primer body region refers to an oligonucleotide region having a base sequence capable of hybridizing to the reverse transcription product or its complementary strand and thereby capable of functioning as a primer in the nucleic acid amplification reaction. Specifically, the sequence is similar to that on the 5'-end side of the reverse transcription product (single-stranded DNA) or is capable of hybridizing to the 3'-end side thereof. Generally, the sequence is a base sequence identical to that on the 5'-end side of the reverse transcription product or a sequence complementary to the base sequence on the 3'-end side thereof. Each of these primer body regions may contain a base deletion or insertion, or a mismatch site as long as it is capable of specifically binding to the reverse transcription product or its complementary strand. The primer body region preferably has a length of 8 or more bases, more preferably 12 or more bases, still more preferably 15 or more bases. The maximum chain length of the primer is not particularly limited, but in view of the cost for synthesis, for example, suitably the chain length is usually 50 or less bases or 40 or less bases.

The tag region of the primer preferably contains a natural nucleotide. The term "natural nucleotide" refers to a nucleotide composed of a natural base (adenine, thymine, guanine, cytosine, or uracil), a sugar moiety (deoxyribose or ribose), and a phosphate group, all of which are not artificially modified. The natural nucleotide may be a D-nucleotide or L-nucleotide. The term "D-nucleotide" refers to a nucleotide containing D-deoxyribose or D-ribose. Likewise, the term "L-nucleotide" refers to a nucleotide containing L-deoxyribose or L-ribose. The tag region containing a natural nucleotide has an effect in that it allows for easy and low-cost synthesis. Moreover, the proportion of natural nucleotides in the tag region of the primer is preferably 5% or more, more preferably 20% or more, still more preferably 50% or more, yet still more preferably 70% or more, most preferably 90% or more. The tag region may have any length, as long as it is long enough to hybridize to a complementary nucleic acid strand. The length is usually 5 bases to 60 bases, preferably 6 bases to 40 bases.

Specifically, preferably, the tag region of the primer has a nucleic acid sequence in the same orientation as the primer body region having a sequence capable of hybridizing to the reverse transcription product or its complementary strand. The primer having a tag region having a nucleic acid sequence in the same orientation as the primer body region has an effect in that it allows for easy and low-cost synthesis. Even when the tag region is not directly linked to the primer body region as in the case where a non-natural compound such as azobenzene is inserted between the tag region and the primer body region, it is preferred that these regions have sequences in the same orientation. Alternatively, the tag region may contain a nucleic acid sequence in the same orientation as the primer body region having a sequence capable of hybridizing to the reverse transcription product or its complementary strand, and a nucleic acid sequence in the opposite orientation.

The phrase "nucleic acid sequence in the same orientation" means that adjacent nucleotides are linked to each other via a phosphodiester bond between the 5' and 3' carbons, not between the 3' carbons or between the 5' carbons, of the sugar moieties of the nucleotides. For example, in the case of the tag region where nucleotides are linked to one another via a phosphodiester bond between the 5' and 3' carbons of the sugar moieties, the nucleotides in the body region are also linked to one another between the 5' and 3' carbons of the sugar moieties.

The polymerase reaction inhibitory region inhibits a nucleic acid extension reaction catalyzed by polymerase, and maintains the single-stranded structure of the region. The primer may contain multiple types of polymerase reaction inhibitory regions and/or contain a plurality of polymerase reaction inhibitory regions. The polymerase reaction inhibitory region may have any structure as long as it can inhibit a nucleic acid extension reaction catalyzed by polymerase. The structure may contain a nucleic acid derivative or a non-nucleic acid derivative.

The nucleic acid derivative is not particularly limited as long as it can inhibit an extension reaction catalyzed by polymerase and maintain the single-stranded structure of the tag region. Examples of the nucleic acid derivative include nucleic acids forming an inverted sequence structure, such as a 5'-5' linkage or a 3'-3' linkage, nucleic acids having a three-dimensional structure that inhibits the progress of polymerase, such as a tight hairpin structure or a pseudoknot structure, L-nucleic acids, 3-deoxy-2-hydroxy-dNs, nucleic acids containing modified bases, nucleic acids containing damaged bases, nucleic acids containing modified phosphate linkages, RNAs, 2'-OMe-Ns, and derivatives of the foregoing.

The terms "hairpin structure" and "pseudoknot structure" refer to stable loop structures formed by pairing with another single-stranded region in the same molecule.

The term "inverted sequence structure" refers to a structure containing a 5'-5' linkage or a 3'-3' linkage. The terms "5'-5' linkage" and "3'-3' linkage" refer to a linkage between the 5' carbon of one deoxyribose and the 5' carbon of another deoxyribose adjacent thereto via a phosphate group, and a linkage between the 3' carbon of one deoxyribose and the 3' carbon of another deoxyribose adjacent thereto via a phosphate group, respectively, in a DNA, as shown in formula (1):

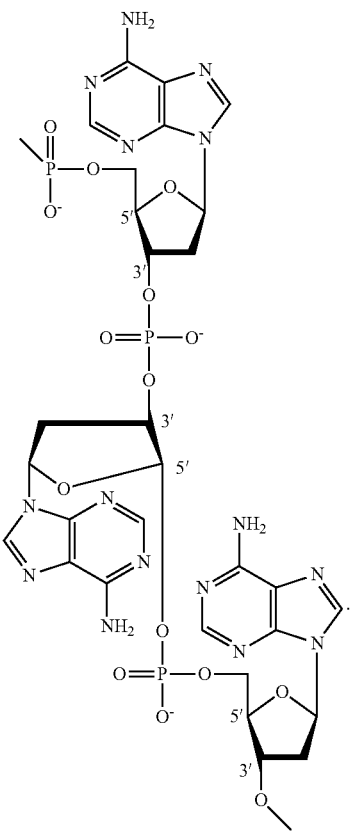

(1)

These linkages are inverted from the normal 5'-3' linkage, and are thus referred to as inverted sequence structures. Specific examples include a structure having two inverted structures so as to be linked to the 5' region of the primer body region (the region having a sequence capable of hybridizing to the reverse transcription product or its complementary strand) via a 5'-5' linkage and linked to the 3' end of the tag region via a 3'-3' linkage. Moreover, the number of inverted structures is not particularly limited as long as at least one inverted structure is present, although an even number is preferred. With an even number of inverted structures, the tag region has a 5' free end as in normal primers. This makes it possible to inhibit a non-specific extension reaction from the tag region and is also effective for detection. Moreover, when the polymerase reaction inhibitory region preferably contains 5 to 60 bases, instead of one base as shown in formula (1), it can function both as a polymerase reaction inhibitory region and a tag region.

The term "L-nucleic acid" refers to an L-DNA or L-RNA or a derivative thereof in which the sugar of the nucleic acid, i.e., deoxyribose or ribose, is an optical isomer of the natural D-form as shown in formula (2):

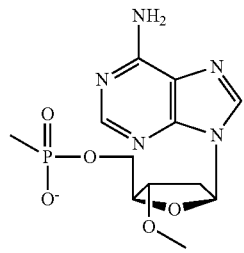

(2)

or formula (3):

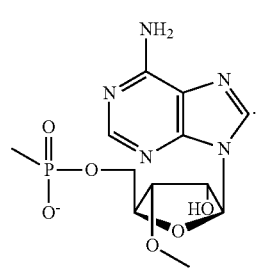

(3)

L-nucleic acids, which are not recognized by commonly used DNA polymerases, do not function as templates in extension reactions. L-DNAs, which form a left-handed double helix, will not hybridize to natural D-nucleic acids but can hybridize only to nucleic acids of the same L-form.

3-Deoxy-2-hydroxy-dNs have a 2'-5' linkage between the 2' carbon of one deoxyribose having no hydroxyl group at the 3' carbon and the 5' carbon of the adjacent deoxyribose as in a 3-deoxy-2-hydroxy-dA shown in formula (4):

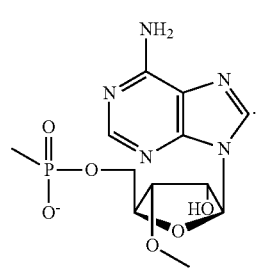

(4)

Due to this structure, they are not recognized by DNA polymerases and thus do not function as templates in extension reactions. In the present invention, the 3-deoxy-2-hydroxy-dN is preferably linked into the primer via a 2'-5' linkage.

The term "nucleic acid containing a modified base" refers to a nucleic acid having a DNA base site modified with biotin, a chromophore, or the like. Examples of the chromophore include, but are not limited to, pyrene, etheno, pyrrolo, perylene, fluorescein, FITC, Cy3, Cy5, TAMRA, Dabcyl, and cyanine dyes. Examples of the nucleic acid containing a modified base include, but are not limited to, amino C6-dA shown in formula (5):

carboxy-dT shown in formula (9):
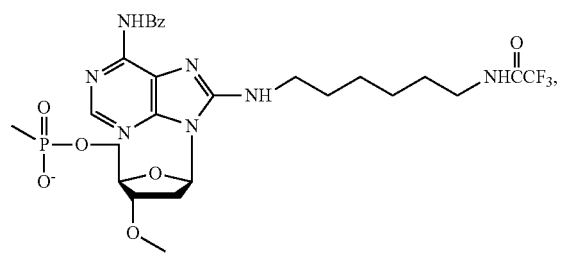
2-thio-dT shown in formula (6):
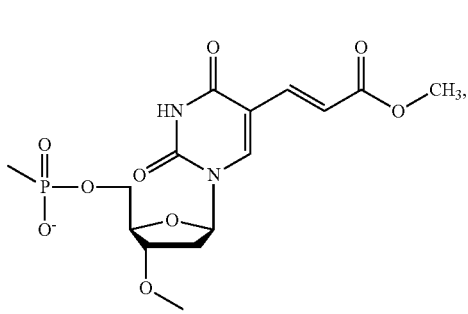
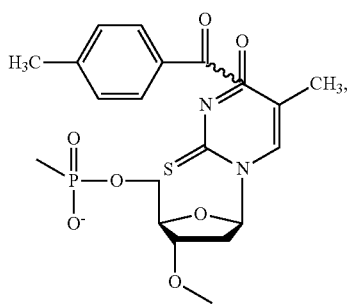
4-thio-dT shown in formula (7):
pyrene-dU shown in formula (10):
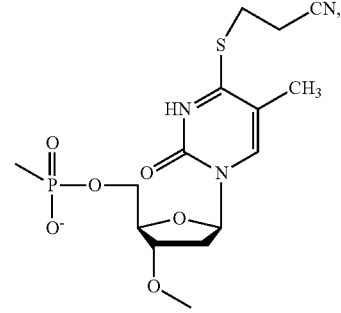
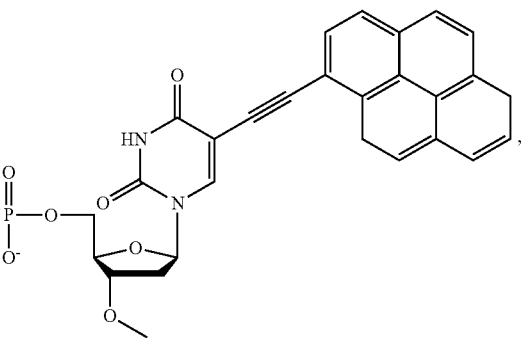
biotin-dT shown in formula (8):
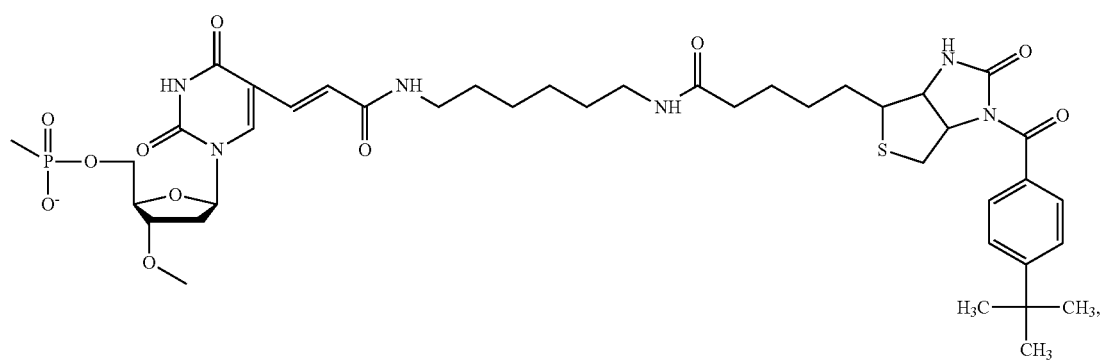

etheno-dA shown in formula (13):
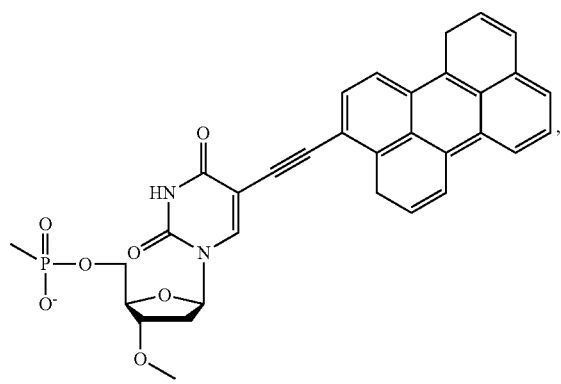
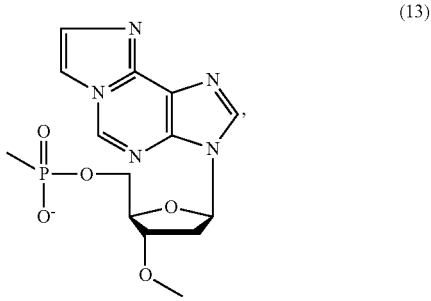
pyrrolo-dC shown in formula (12):
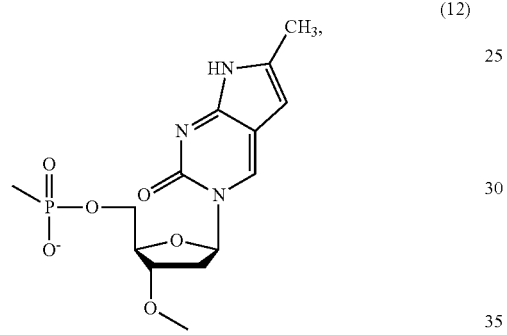
FITC-dT shown in formula (14):
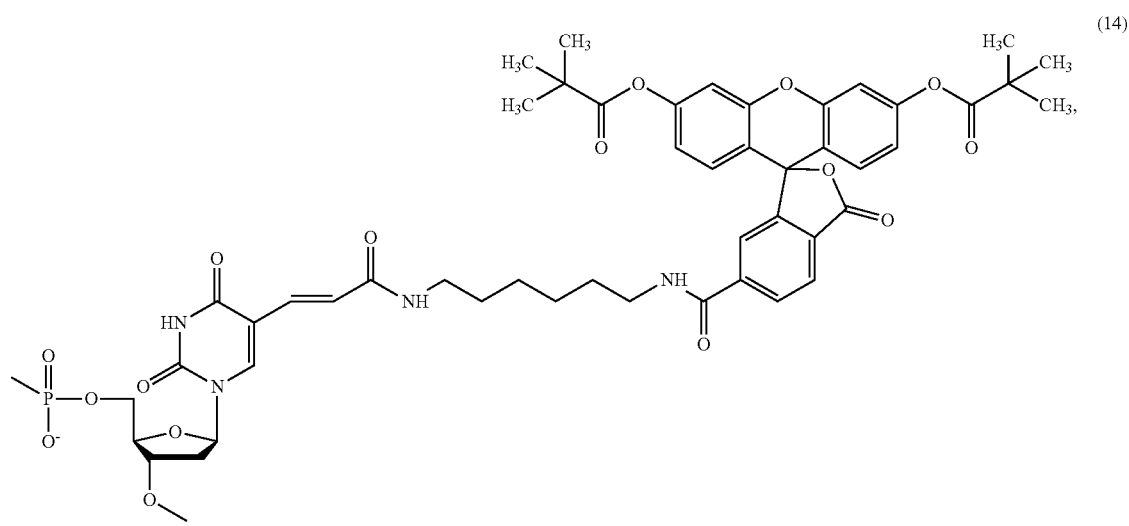

TAMRA-dT shown in formula (15):

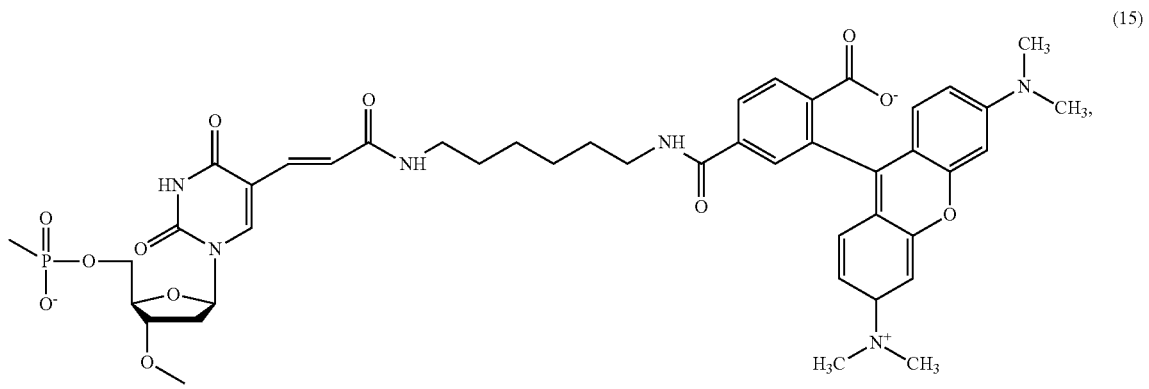

Dabcyl-dT shown in formula (16):

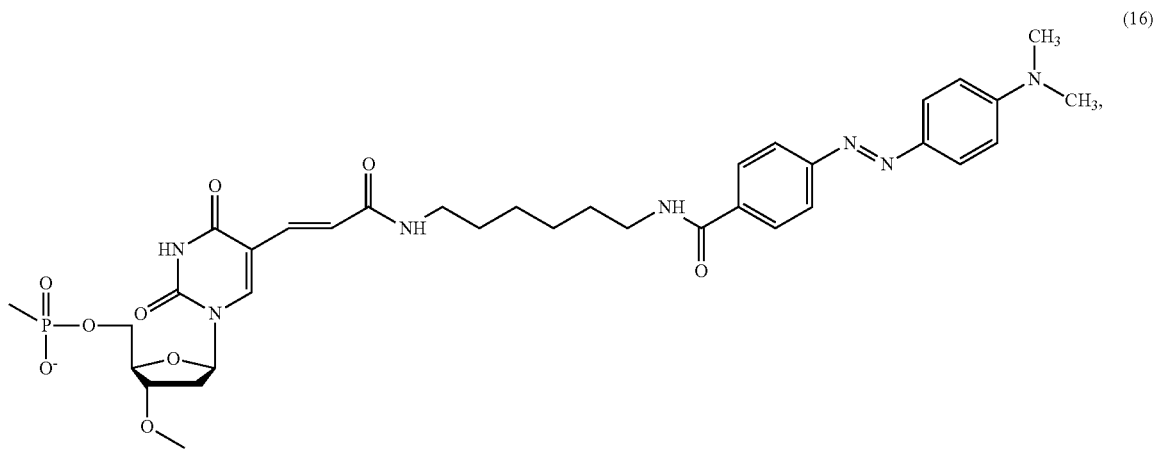

BHQ-1-dT, Cy3-dT, and Cy5-dT. These nucleic acids are not recognized by DNA polymerases because of the steric hindrance arising from the modifications in the base moiety and thus do not function as templates in extension reactions.

The term "nucleic acid containing a damaged base" refers to an abasic nucleic acid or a nucleic acid containing a modified base, such as abasic nucleotides (AP site: apurinic base, apyrimidinic base), dSpacer shown in formula (17):

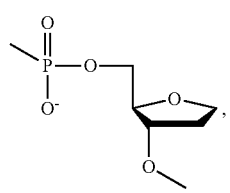

Abasic shown in formula (18):

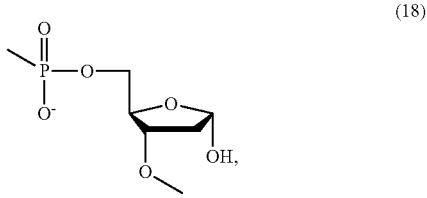

and 5-hydroxymethyl-dNs. These nucleic acids are not recognized by commonly used DNA polymerases and thus do not function as templates in extension reactions.

The term "nucleic acid containing a modified phosphate linkage" refers to a nucleic acid whose phosphate groups are partially substituted by other atoms or molecules, such as phosphorothioates (S-oligos) shown in formula (19):

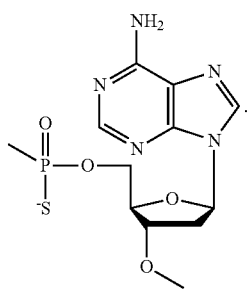

(19)

These nucleic acids are not recognized by DNA polymerases and thus do not function as templates in extension reactions.

The term "RNA" refers to a nucleic acid whose sugar is ribose as shown in formula (20):

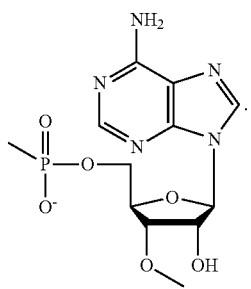

(20)

Such nucleic acids are not recognized by commonly used DNA polymerases and thus do not function as templates in extension reactions.

The term "2'-OMe-N" refers to a nucleic acid whose sugar moiety is modified as in 2'-OMe-G as shown in formula (21):

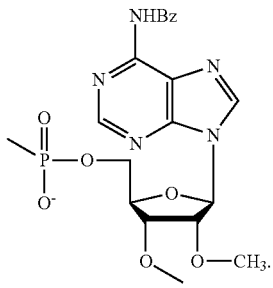

(21)

Such nucleic acids are not recognized by DNA polymerases and thus do not function as templates in extension reactions.

Examples of the non-nucleic acid derivative include D-threoninol scaffolds, aliphatic chains such as carbon chains ($C_n$) and PC spacer, PEG chains (($CH_2CH_2O)_n$), disulfide-containing chains ($C_nSSC_n$), PNA, dithiol phosphoramidite, and derivatives of the foregoing. The non-nucleic acid derivative is not particularly limited as long as it can inhibit a nucleic acid extension reaction catalyzed by polymerase and maintain the single-stranded structure of the region. Such non-nucleic acid molecules are not recognized by DNA polymerases because their structures are different from nucleic acids, and thus do not function as templates in DNA extension reactions.

The term "D-threoninol scaffold" refers to a structure in which nucleic acids are linked via threoninol as shown in formula (22):

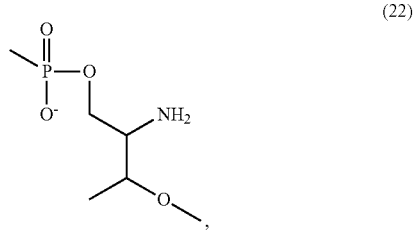

(22)

and various types of molecules can be inserted into the amino group of threoninol. Any molecule can be inserted as long as it can be coupled via an amino group. Examples of molecules that may be inserted include chromophores such as pyrrolo, pyrene, etheno, perylene, FITC, TET, HEX, JOE, Cy3, Cy5, Dabcyl, and BHQ dyes, biotin, EDTA, azobenzene shown in formula (23):

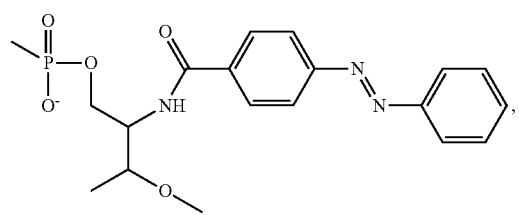

(23)

and the like.

The term "aliphatic chain" refers to a continuous carbon chain represented by $C_n$ or a derivative thereof. Examples include C3 linker shown in formula (24):

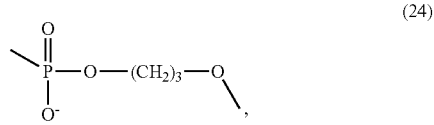

(24)

C6 linker, and C12 linker shown in formula (25):

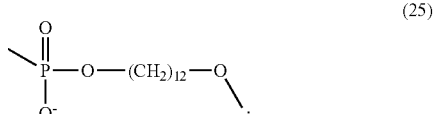

(25)

The value of n is not particularly limited. Moreover, examples of the derivative include PC Sspacer shown in formula (26):

(26)

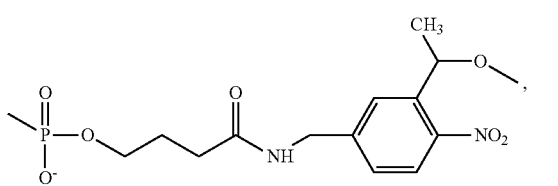

and other structures.

The term "PEG chain" refers to a structure in which polyethylene glycol units are linked as represented by $(CH_2CH_2O)_n$, or a derivative thereof. Examples include Spacer 9 (triethyleneglycol spacer) shown in formula (27):

(27)

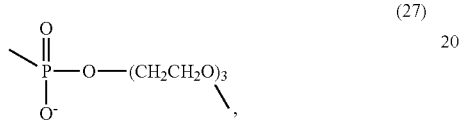

and Spacer 18 (hexa-ethyleneglycol spacer) shown in formula (28):

(28)

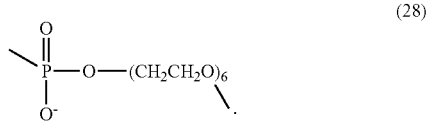

The value of n is not particularly limited.

The term "disulfide-containing chain" refers to a structure containing a disulfide bond represented by $(C_nSSC_n)$. Examples include a chain having three carbon atoms shown in formula (29):

(29)

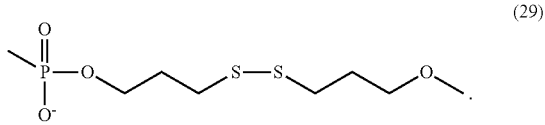

Moreover, as long as the chain contains a disulfide bond, it may have an aliphatic chain, PEG chain, or the like on each side of the disulfide bond. Other examples of the disulfide-containing chain include dithiol phosphoramidite shown in formula (30):

(30)

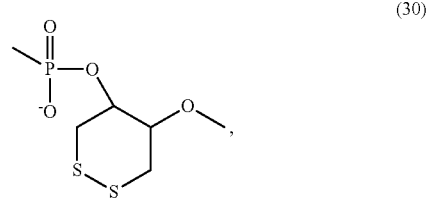

and the like.

The term "PNA" refers to a molecule having a structure similar to DNA or RNA but having a peptide bond-containing backbone in which N-(2-aminoethyl)glycine units are linked via an amide bond. Further, purine and pyrimidine rings, which correspond to nucleic acid bases, are linked to the backbone via a methylene group and a carbonyl group.

The term "BNA (LNA)" refers to a nucleic acid shown in formula (31):

(31)

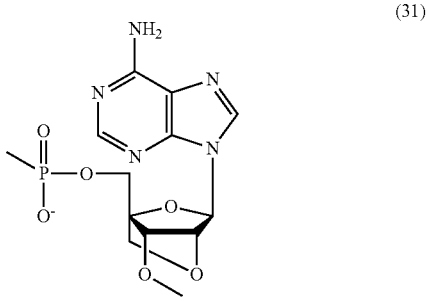 [SMILES: COC1[C@@H]2OC[C@]1(COP(C)(=O)[O-])O[C@H]2n1cnc2c(N)ncnc21]

which is artificially synthesized by modifying the sugar moiety of DNA or RNA so as to form a bridge.

In the case of a tag region that consists only of natural nucleotides and has a nucleic acid sequence in the same orientation as the primer body region, a polymerase reaction inhibitory region is usually necessary between the tag region and the primer region. In contrast, in the case of a tag region that is incapable of serving as a template in reactions catalyzed by DNA polymerases and thus is not made double-stranded by the nucleic acid amplification reaction as in the case of L-nucleic acids and artificial nucleic acids, the tag region also functions as a polymerase reaction inhibitory region. Moreover, the primer in the present invention may contain one or a combination of two or more of stable loop structures such as a hairpin structure and a pseudoknot structure, non-natural nucleic acids such as L-nucleic acids and artificial nucleic acids, and non-nucleic acid molecules such as aliphatic chains.

The primer may be labeled with various molecules generally used for labeling oligonucleotides. Examples of such molecules include enzymes, magnetic particles, fluorescent pigments, and radioisotopes. These may be used alone or in combination of two or more thereof.

The primers thus designed may be prepared by any known method. Specifically, the designed primers can be easily obtained with DNA synthesizers or from custom synthesis services.

The nucleic acid amplification method is not particularly limited as long as an amplified double-stranded DNA fragment having a single-stranded region at the end can be produced by the method using the primers described above. An example of the method is PCR. Isothermal amplification techniques such as LAMP and ICAN may also be used.

In the case where the nucleic acid amplification method is PCR, the pair of reverse and forward primers for PCR may be designed such that these two primers contain different polymerase reaction inhibitory regions from each other and one of the regions is used as a labeling substance-binding region; or such that only one primer contains a polymerase reaction inhibitory region and the other primer is modified with biotin or the like to form a labeling substance-binding region instead of incorporating a polymerase reaction inhibitory region.

The PCR conditions are not particularly limited as long as a target region of a cDNA is amplified by PCR using the reverse transcription product as a template and the primer set. Specifically, the polymerase used in PCR is not particularly limited, but it is preferably a heat-stable DNA polymerase, more preferably a heat-stable DNA polymerase that does not substantially have 3'-to-5' exonuclease activity. Examples of such heat-stable DNA polymerases include, but are not limited to, Ex-Taq (Takara Bio, Inc.). Likewise, the PCR conditions such as temperature, time, and buffer composition are not particularly limited, and may be appropriately chosen according to the DNA polymerase selected, the sequences of the primers, the length of the target sequence, and other factors. The length of the DNA to be amplified by the nucleic acid amplification reaction is preferably 20 or more bases, more preferably 40 or more bases. A length of less than 20 bases tends to result in increased non-specific amplification.

Carrying out PCR in a conventional manner using the primer set can produce an amplified double-stranded DNA product in which a single-stranded region is added to the end of the reverse transcription product.

Figure 4:
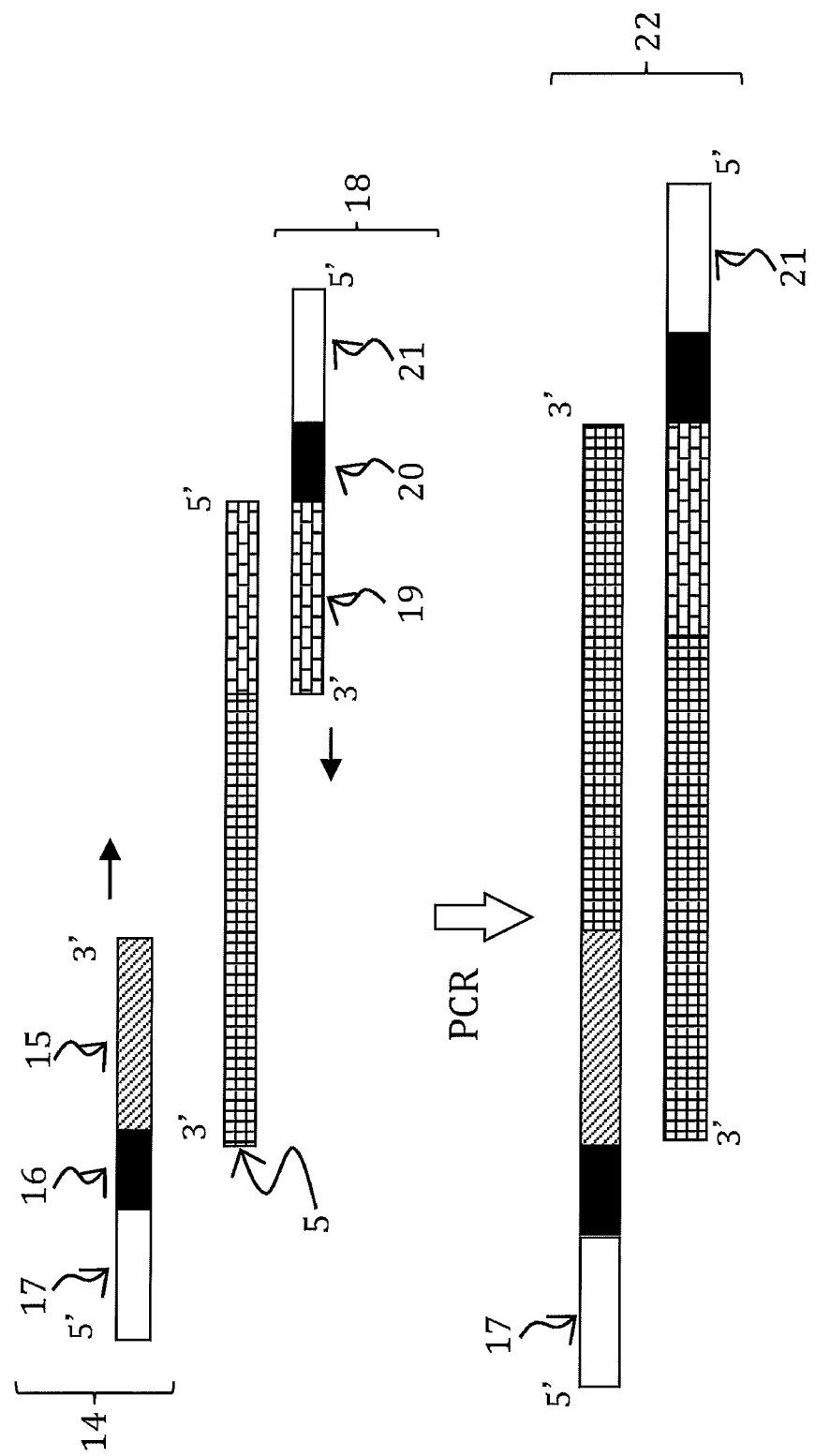
FIG. 4 is a conceptual diagram of a method for synthesizing a double-stranded nucleic acid having a single-stranded region at each end from the reverse transcription product produced in FIG. 1.

FIG. 4 is a schematic diagram of an example of an amplification reaction using the reverse transcription product produced by the method shown in FIG. 1 as a template and a primer set containing a primer body region, a polymerase reaction inhibitory region, and a tag region.

A forward primer 18 contains a primer body region 19 having a sequence identical to a 5'-end portion of a reverse transcription product 5, and also contains a polymerase reaction inhibitory region 20 and a tag region 21 on the 5'-end side of the primer body region 19. A reverse primer 14 contains a primer body region 15 having a sequence complementary to a 3'-end portion of the reverse transcription product, and also contains a polymerase reaction inhibitory region 16 and a tag region 17 on the 5'-end side of the primer body region 15. These tag regions attached to the respective primers usually have different sequences from each other. When PCR is carried out using the primer set, since the tag regions added to the primers are not substantially involved in PCR, an amplified DNA product 22 having a single-stranded region at each end can be obtained. The "amplified DNA fragment having a single-stranded region at each end" refers to an amplified DNA product having a double-stranded DNA portion identical to the target nucleic acid region and also having a single-stranded region as a tag portion at each 5' end of the DNA portion, as shown in FIG. 4. In other words, the amplified DNA fragment shown in FIG. 4 is an amplified double-stranded DNA fragment having a single-stranded region formed of a non-modified nucleic acid at each end, and the single-stranded regions at both ends have sequences in the same orientation as the respective adjacent DNA strands.

Figure 5:
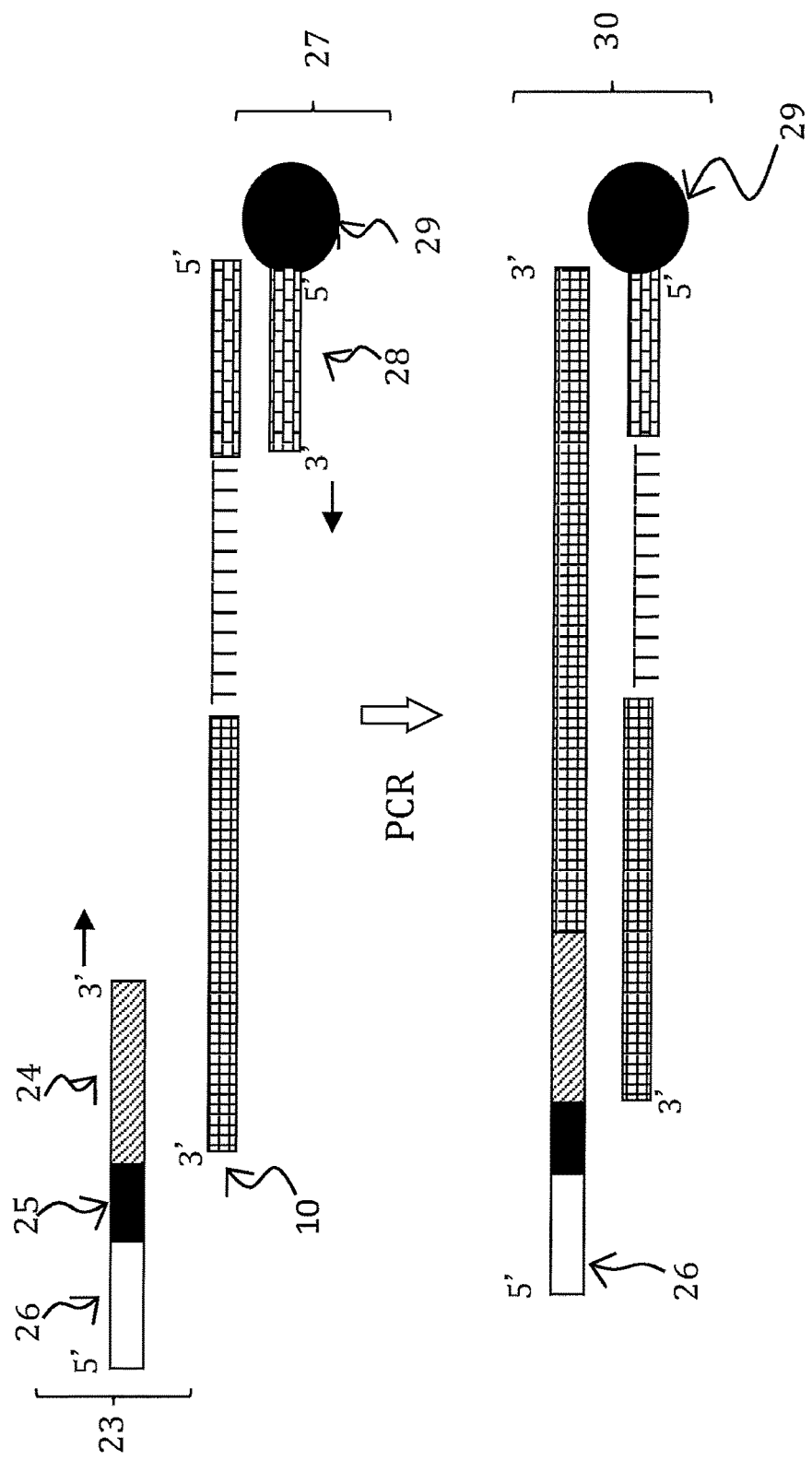
FIG. 5 is a conceptual diagram of a method for synthesizing, from the reverse transcription product produced in FIG. 2, a double-stranded nucleic acid having a single-stranded region at one end and a labeling substance-binding region containing biotin or the like at the other end.

FIG. 5 is a schematic diagram of an example of an amplification reaction using the reverse transcription product produced in FIG. 2 as a template, a primer containing a primer body region, a polymerase reaction inhibitory region, and a tag region, and a labeling substance-binding primer. A forward primer 27 contains a primer body region 19 having a poly(T) sequence and a sequence identical to a 5'-end portion of a reverse transcription product 10, and a labeling substance-binding region 29 on the 5'-end side of the primer body region. A reverse primer 23 contains a primer body region 24 having a sequence complementary to a 3'-end portion of the reverse transcription product, and also contains a polymerase reaction inhibitory region 25 and a tag region 26 on the 5'-end side of the primer body region 24. When PCR is carried out using the primer set, since the tag region added to the primer is not substantially involved in the PCR, an amplified DNA product 30 having a single-stranded region at an end can be obtained. The "amplified DNA fragment having a single-stranded region at an end" refers to an amplified DNA product having a double-stranded DNA portion having a sequence identical to the reverse transcription product and also having a single-stranded region as a tag portion at one 5'-end of the DNA portion, as shown in FIG. 5. In other words, the amplified DNA fragment shown in FIG. 5 is an amplified double-stranded DNA fragment having a single-stranded region formed of a non-modified nucleic acid at an end, and the single-stranded region at the end has a sequence in the same orientation as the adjacent DNA strand.

The single-stranded region of the amplified double-stranded DNA fragment is used to form a hybridization complex. The term "hybridization" means that molecules containing nucleic acids complementarily form a complex, such as DNA/DNA and other complexes including DNA/RNA, DNA/PNA, and L-DNA/L-DNA complexes. In the nucleic acid detection method of the present invention, the amplified DNA product obtained in the nucleic acid amplification step can be used in a hybridization reaction without any treatment for conversion into single-strands such as heat treatment because the amplified double-stranded DNA fragment has a single-stranded region.

An oligonucleotide probe immobilized on a capture carrier (solid phase) can be hybridized to the single-stranded region of the amplified double-stranded DNA fragment having a single-stranded tag region at the end. Further, the amplified double-stranded DNA fragment is preferably capable of binding to a labeling substance. The binding between the amplified double-stranded DNA fragment and the labeling substance may be achieved via the single-stranded region or the labeling substance-binding region. A complex consisting of the amplified double-stranded DNA fragment, the oligonucleotide probe, and the labeling substance is referred to as a ternary complex. The binding order of these three is not particularly limited.

The length of the oligonucleotide probe is not particularly limited as long as it is long enough to hybridize to the single-stranded region of the amplified double-stranded DNA fragment. The length is preferably 5 or more bases, more preferably 10 to 40 bases.

The structure of the labeling substance-binding region is not particularly limited as long as it can bind to a labeling substance. For example, the labeling substance-binding region may be a sequence containing a target-binding substance such as biotin. When biotin is used as a target-binding substance, a streptavidin-bound labeling substance can be bound to the labeling substance-binding region via interaction between biotin and streptavidin.

In another embodiment, the single-stranded region may be used as a labeling substance-binding region. In this case, a labeling substance can be indirectly bound to the labeling substance-binding region via hybridization of the single-stranded region to the oligonucleotide probe labeled with the labeling substance. The length of the oligonucleotide probe is not particularly limited as long as it is long enough to hybridize to the single-stranded region of the amplified double-stranded DNA fragment. The length is preferably 5 or more bases, more preferably 10 to 40 bases.

The labeling substance is not particularly limited as long as it allows the amplified double-stranded DNA fragment to be detected. Preferably, the labeling substance is a colored carrier that allows for visual detection of the amplified double-stranded DNA fragment. Examples of such colored carriers include colored particles and enzyme- or pigment-bound carriers. Colored particles are preferred among these.

Examples of the colored particles include colloidal particles of metals such as gold, silver, copper, and platinum; colored latex obtained by coloring latex with pigments, dyes or the like; and silica nanoparticles which are silica (silicon dioxide) particles with pigment molecules immobilized inside. Colloidal gold particles and colored (e.g. blue, red) latex particles made of water-dispersible polymers are preferred among these. The use of such colored particles further facilitates visual analysis of the amplified DNA fragment. In particular, when multiple analytes are desired to be simultaneously detected, the use of different colored particles for each analyte facilitates simultaneous visual analysis of the multiple analytes.

When colored particles are used, the particle size is not particularly limited. Preferred colored particles are ones that have less adverse effects on the formation of the ternary complex and on the capture of the target sequence-containing amplified product on the solid phase and also exhibit good color development in the detection. The particle size of colored particles is selected from particle sizes smaller than the pore size of a later-described chromatographic medium. Specifically, the particle size is usually 500 nm or less, and in particular preferably 0.1 nm to 100 nm, more preferably 1 nm to 50 nm.

When an enzyme is used as a colored carrier, such an enzyme is preferably a protein that catalyzes a reaction of a substrate to develop a color or emit light. Examples include peroxidases, alkaline phosphatases, and luciferases. The enzyme is not particularly limited to these examples as long as it allows for detection by the naked eye.

The conditions of hybridization of the single-stranded region at the end of the amplified double-stranded DNA fragment to the oligonucleotide probe are not particularly limited as long as hybridization occurs. Preferably, hybridization is carried out in 10 mM phosphate buffer at room temperature. Adding a salt such as sodium chloride under these conditions increases hybridization efficiency.

The presence of the target nucleic acid can be analyzed by detecting the labeling substance in the ternary complex formed in an identifiable zone on the capture carrier (solid phase). Preferably, the presence of the target nucleic acid is visually analyzed. According to the detection method of the present invention, the amplified product obtained by the nucleic acid amplification reaction can be used directly in a hybridization reaction without any treatment for conversion into single-strands such as heat denaturation. Further, it is possible to visually analyze the presence of the target nucleic acid in a simple and rapid manner without the need for special equipment.

The nucleic acid detection method involving the formation of the ternary complex is preferably carried out on a nucleic acid detection device and more preferably on a chromatography device.

Figure 6:
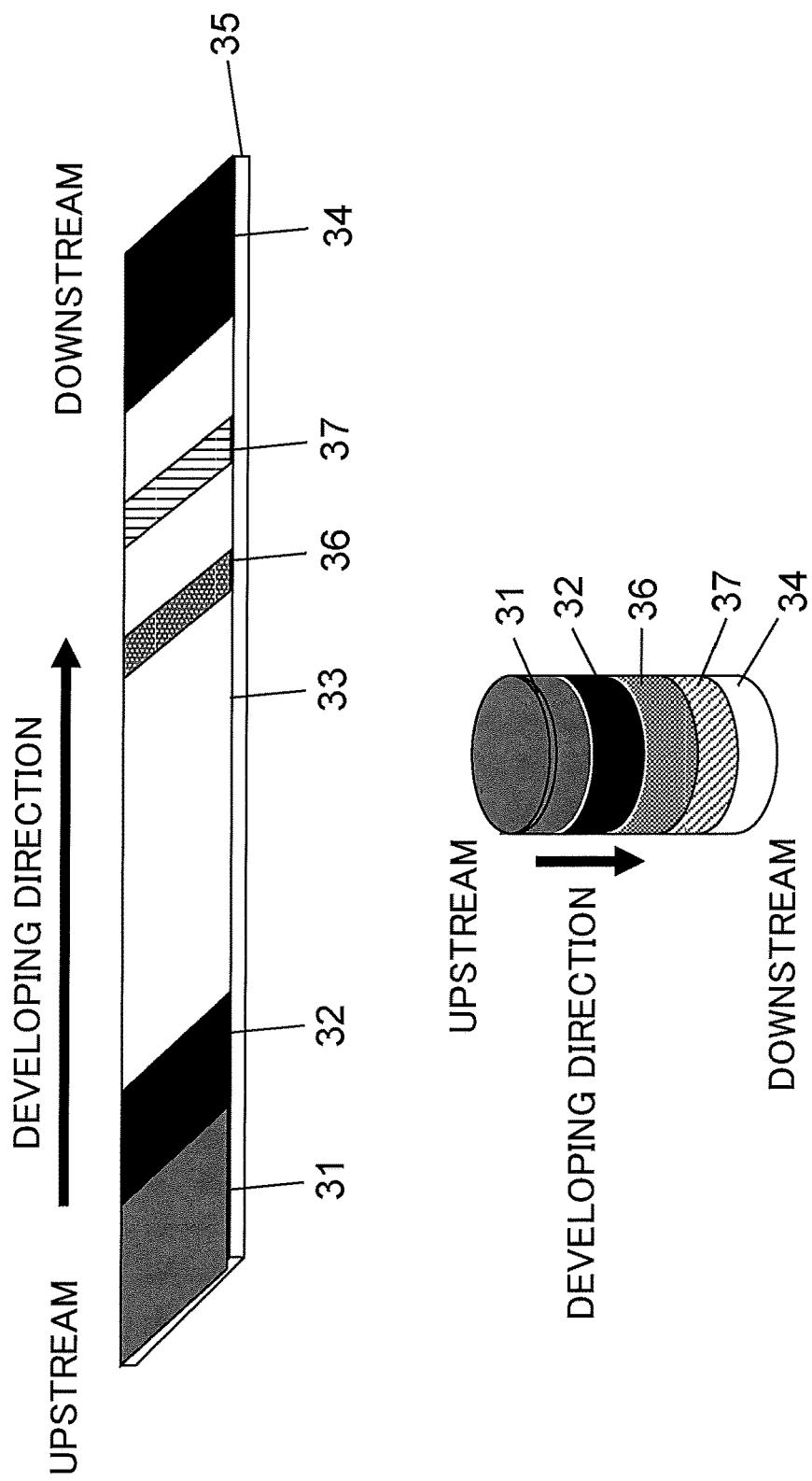
FIG. 6 is a schematic view showing examples of nucleic acid chromatography devices.

FIG. 6 shows a nucleic acid chromatography device that includes a substrate member 35 on which a sample pad 31 (a carrier to which an amplified double-stranded DNA fragment is to be applied), a conjugate pad 32 (a carrier in which a colored carrier is placed), a carrier 33 carrying a capture oligonucleotide (a chromatographic medium), and an absorption pad 34 are bonded with an adhesive or other means. The carrier 33 is provided with a test line 36 along which the capture oligonucleotide is applied, and a control line 37. In the case where a colored carrier-bound oligonucleotide is mixed with a developing solution, the conjugate pad 32 may not be used.

Chromatography is preferably carried out by a method including the following steps (a) to (c) to detect an amplified double-stranded DNA fragment: (a) placing the amplified double-stranded DNA fragment in a zone on the nucleic acid detection device which is different from a zone where the oligonucleotide probe is immobilized; (b) diffusing the amplified double-stranded DNA fragment on the device with a solvent toward the zone where the oligonucleotide probe is immobilized; and (c) hybridizing the amplified double-stranded DNA fragment to the oligonucleotide probe in the zone where the oligonucleotide probe is immobilized. The present invention also relates to a nucleic acid detection device for use in the nucleic acid detection method, the device including a zone where the amplified double-stranded DNA fragment is placed; a chromatographic carrier carrying the oligonucleotide probe that binds to the amplified double-stranded DNA fragment; and an oligonucleotide probe labeled with a labeling substance.

For example, in the case of the nucleic acid chromatography device of FIG. 6, the amplified double-stranded DNA fragment is placed on the sample pad 31 in step (a). In step (b), the amplified double-stranded DNA fragment is diffused in the direction of the arrow. In step (c), the amplified double-stranded DNA fragment is captured through hybridization to the oligonucleotide probe immobilized on the test line 36.

Preferably, the method further includes before step (c) the step of binding the amplified double-stranded DNA fragment to the labeling substance. For example, in the case of the nucleic acid chromatography device of FIG. 6, the amplified double-stranded DNA fragment is bound to the labeling substance on the conjugate pad 32.

The chromatography preferably includes the following steps (d) to (h): (d) placing the amplified double-stranded DNA fragment and the labeling substance in respective zones on the nucleic acid detection device which are different from a zone where the oligonucleotide probe is immobilized; (e) diffusing the amplified double-stranded DNA fragment with a solvent toward the zone where the labeling substance is placed; (f) binding the amplified double-stranded DNA fragment to the labeling substance in the zone where the labeling substance is placed; (g) diffusing a complex formed by binding in step (f) on the device toward the zone where the oligonucleotide probe is placed; and (h) hybridizing the complex to the oligonucleotide probe in the zone where the oligonucleotide probe is immobilized.

For example, in the case of the nucleic acid chromatography device of FIG. 6, in step (d), the amplified double-stranded DNA fragment is placed on the sample pad 31 while the labeling substance is placed on the conjugate pad 32. In step (e), the amplified double-stranded DNA fragment is diffused from the sample pad 31 in the direction of the arrow. In step (f), the amplified double-stranded DNA fragment is bound to the labeling substance on the conjugate pad 32. In step (g), a complex formed by binding of the amplified double-stranded DNA fragment and the labeling substance is diffused in the direction of the arrow. In step (h), the complex is hybridized to the oligonucleotide probe on the test line 36.

On the test line on the membrane, an oligonucleotide probe having a sequence complementary to the tag region of the amplified double-stranded DNA fragment is immobilized as a capture oligonucleotide probe. The capture oligonucleotide probe may be bound to the membrane directly or via a functional group or a substance. Examples of such mediating substances include, but are not limited to, peptides, proteins, and nucleic acids. When avidin is used as a mediating substance, the capture oligonucleotide needs to be modified with biotin.

A substance for capturing a colored carrier is immobilized on the control line of the membrane. The colored carrier-capturing substance is not particularly limited, and examples include oligonucleotide probes, peptides, and proteins. When a labeling substance bound to an oligonucleotide probe is used, the colored carrier-capturing substance for the control line is also an oligonucleotide probe. Accordingly, the labeling substance is reliably captured when the sample solution is developed. The colored carrier-capturing substance for the control line may be similarly bound to the membrane directly or via a functional group or a substance as described above. Examples of such mediating substances include, but are not limited to, peptides, proteins and nucleic acids. When avidin is used as a mediating substance, the capture substance needs to be modified with biotin.

The presence of the target nucleic acid in the sample can be determined visually based on color changes of the test line. At the same time, whether the development and the color reaction are normally carried out can be determined visually based on color changes of the control line. The term "visually" means that the color is determined by the naked eye. Moreover, in the present invention, since the color intensity of the test line correlates with the concentration of the target nucleic acid, it is possible to quantitate the concentration of the target nucleic acid by measuring the intensity of the color developed on the test line with a device such as a chromatoreader.

Examples of the chromatographic medium include paper filters such as qualitative filters, quantitative filters, phase separating filters, glass fiber filters, silica fiber filters, and composite fiber filters. Other examples include filters made of celluloses, e.g. nitrocellulose or cellulose acetate, synthetic resin films such as polyethersulfone membranes, and porous gels such as silica gel, agarose, dextran, and gelatin. Nylon membranes can also be suitably used. In practical use, the form and size of the chromatographic medium are not particularly limited as long as they are suitable for operation and observation of the reaction results.

These carriers may be modified in various ways to improve hydrophilicity or affinity for compounds. For further simplification of the operation, the back surface of the chromatographic medium whose opposite surface is provided with reaction sites is preferably provided with a support made of a material such as plastic.

The developing direction in the device is not particularly limited, and may be horizontal or vertical as shown in FIG. 6. Since the solvent used in the nucleic acid amplification reaction can serve as a developing solvent, the reaction solution obtained after the nucleic acid amplification reaction can be directly dropped to the sample pad 32 shown in FIG. 6. Alternatively, it is also possible to add a separate developing solution to the reaction solution obtained after the amplification reaction and add the mixture to the sample pad. Any liquid developing solvent can be used. Examples include phosphate buffer and Good's buffers such as Tris buffer. Moreover, the solvent may contain a salt, surfactant, protein, or nucleic acid dissolved therein.

Figure 7:
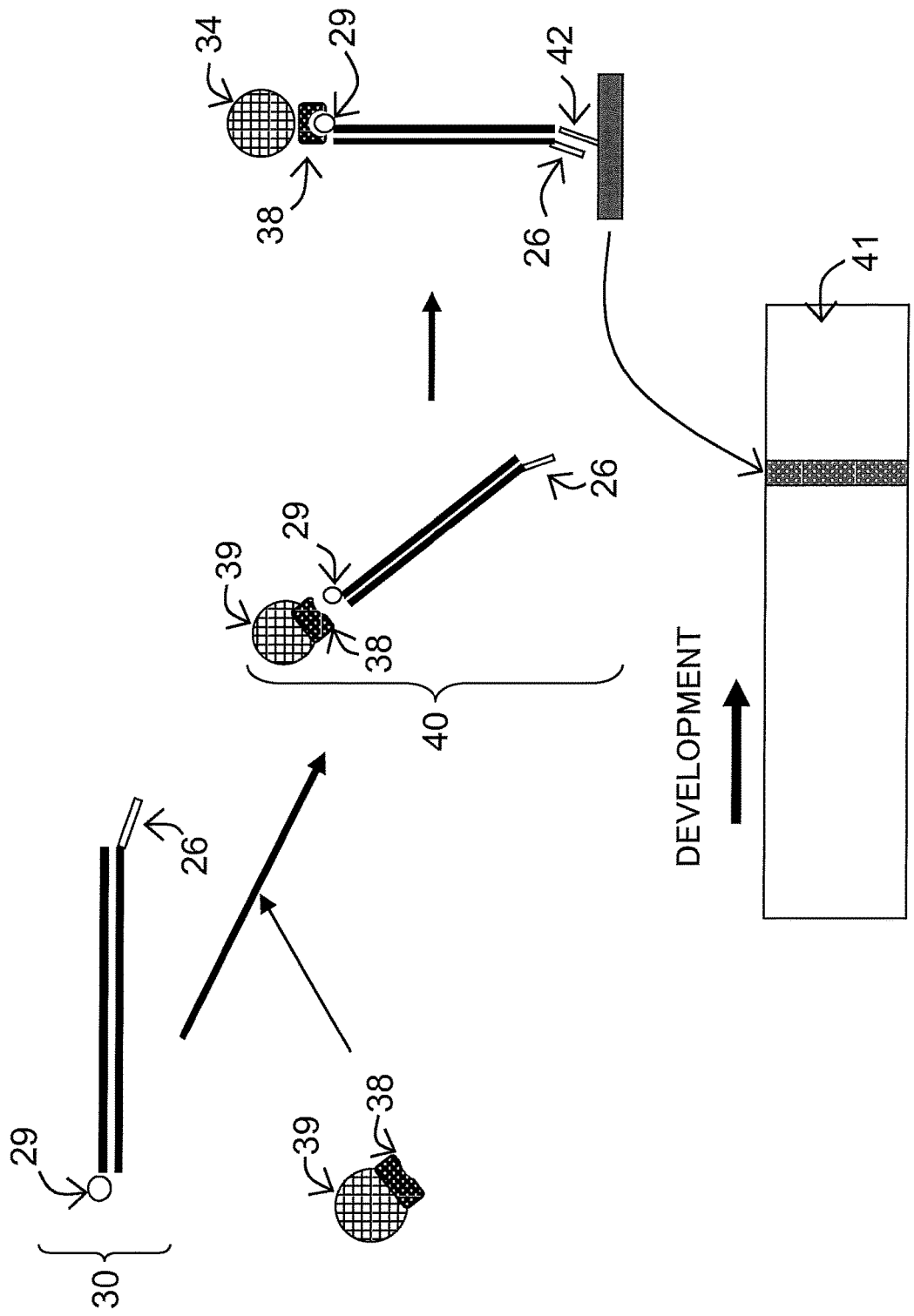
FIG. 7 is a conceptual diagram of the principle of PCR product detection.

With reference to FIG. 7, the formation of a ternary complex on a chromatographic carrier is described as an exemplary embodiment of the present invention. An amplified DNA fragment 30 obtained in the nucleic acid amplification step is used in the subsequent complex formation step without being subjected to any treatment such as conversion into single-strands, e.g. heat treatment. A colored carrier 39 to which a substance 38 capable of specifically binding to a labeling substance-binding region 29 of the DNA fragment has been bound binds to the amplified DNA fragment 30 to form a first complex 40. The complex 40 may be formed prior to the application to the development medium such as in a PCR vessel, or may be formed by applying the amplified DNA fragment to the carrier and allowing the amplified DNA fragment to move by capillary action to pass through the carrier that has been coated with the labeling substance and dried.

The complex 40 comes into contact, on the development medium, with a capture oligonucleotide probe 42 that has been bound in advance to an identifiable zone on a chromatographic medium 41 made of a material such as a porous membrane. The capture oligonucleotide probe 42, which has a sequence complementary to a single-stranded tag sequence 26 of the amplified DNA fragment, hybridizes to the complex 40 to form a ternary complex.

The order of procedures for forming such a ternary complex is not particularly limited. Preferably, the amplified DNA fragment binds to the labeling substance to form a complex 40, which then form a complex with the capture oligonucleotide probe. Alternatively, a ternary complex may be formed by developing the labeling substance after the amplified DNA fragment is enriched using the capture oligonucleotide probe on the development medium.

Figure 8:
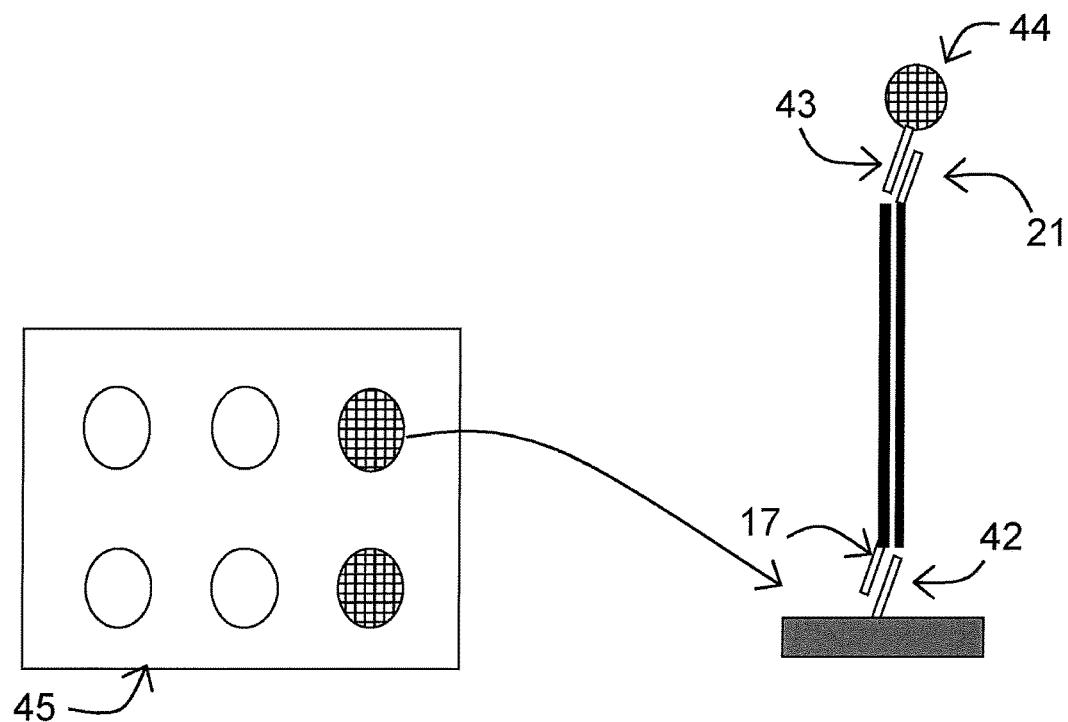
FIG. 8 is a schematic view of an example of a microarray (DNA chip).
Figure 9:
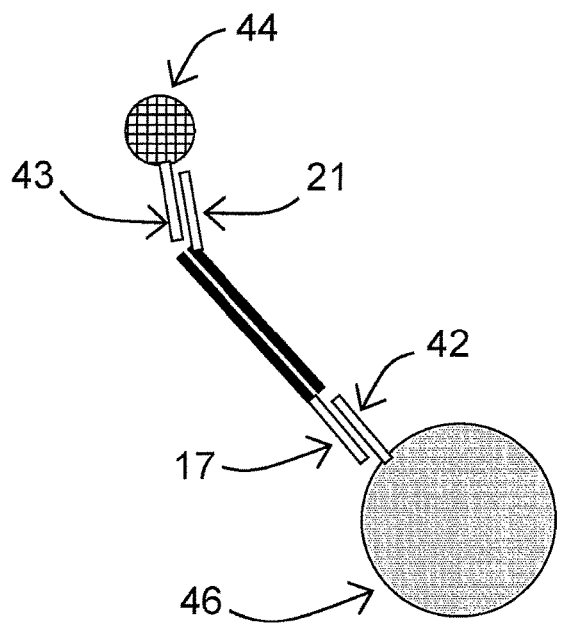
FIG. 9 is a schematic view of an example of a bead carrier.

FIGS. 8 and 9 each show an example of a device for detecting an amplified DNA fragment having a single-stranded region at each end in which one single-stranded tag region is used as a labeling substance-binding region as shown in FIG. 4.

An exemplary embodiment of the nucleic acid detection device other than the chromatography device is a microarray (DNA chip) shown in FIG. 8. A ternary complex can be formed by hybridization in wells on a microarray 45 in which a capture oligonucleotide is immobilized.

Alternatively, the device may be a bead form as shown in FIG. 9. A ternary complex can be formed by hybridization on a bead carrier 46 carrying a capture oligonucleotide.

The nucleic acid detection method and the nucleic acid detection device of the present invention can be used in various techniques involving nucleic acid amplification processes. In other words, they can be used in various techniques in various fields which involve detection of amplified DNA fragments (e.g. PCR products) obtained by nucleic acid amplification methods. Specifically, they can be used in, for example, molecular biology research, detection of pathogens, detection of contaminants such as allergens in foods, food quality control (inspection of mislabeled foods and genetically modified foods), livestock control, detection of single nucleotide polymorphisms (hereinafter also referred to as "SNPs"), and screening of diseases such as cancer. Accordingly, the present invention encompasses methods for detecting pathogenic infections, for detecting contaminants (e.g. allergens) in foods, for food quality control, for livestock control, and for detecting single nucleotide polymorphisms, and other methods in which the nucleic acid detection method of the present invention is included as one step.

As embodiments of application of the present invention, a pathogen detection method and an allergen detection method according to the present invention are described in detail below.

The pathogen detection method according to the present invention may be any method that includes the step of detecting a gene specific to a pathogen by the nucleic acid detection method of the present invention. The pathogen is not particularly limited, and specific examples include pathogenic bacteria, pathogenic viruses, food poisoning bacteria, and bacteria and viruses causing hospital infections. More specifically, there may be mentioned, for example, viruses such as hepatitis C virus (HCV), cytomegalovirus (CMV), Epstein-Barr virus (EBV), herpesviruses, and human immunodeficiency virus (HIV); bacteria such as *Escherichia coli* (e.g. O157), *Mycobacterium tuberculosis, Salmonella typhi, salmonella* bacteria, and *Vibrio parahaemolyticus*; and microorganisms such as *mycoplasma*.

More specifically, in the pathogen detection method according to the present invention, the nucleic acid detection method is used to determine whether a gene specific to a pathogen is present in, for example, a DNA sample prepared from a sample to be assessed for the presence of the pathogen. Alternatively, the sample to be assessed for the presence of the pathogen may be directly used as a template for nucleic acid amplification without preparing a DNA sample. For example, in the case where the pathogen to be detected is a bacterium such as *Escherichia coli*, a bacterial colony suspension can be used as a template. Then, if a gene specific to the pathogen is detected, the sample is determined to contain the pathogen. In this manner, it is possible to determine whether a sample contains a pathogen in a simple and highly accurate manner without the need for special equipment. In other words, the pathogen detection method according to the present invention can be used for the diagnosis of microbial infections.

The allergen detection method according to the present invention may be any method that includes the step of detecting a gene encoding an allergen by the nucleic acid detection method of the present invention. The allergen is not particularly limited, and specific examples include allergens contained in foods. More specific examples include egg albumen allergens, milk allergens, wheat allergens, buckwheat allergens, and peanut allergens. More specifically, in the allergen detection method according to the present invention, the nucleic acid detection method is used to determine whether a gene encoding an allergen derived from a source such as egg, milk, wheat, buckwheat, or peanut is present in, for example, a DNA sample prepared from a food. Then, if such a gene is detected, the food is determined to contain an ingredient containing the allergen.

In this manner, it is possible to determine whether a sample such as a food sample contains an allergen-containing ingredient in a simple and highly accurate manner without the need for special equipment. It should be noted that the allergen origin is not limited to those mentioned above. For example, grains from which allergens may originate include any type of rice, corn, foxtail millet, proso millet, Japanese barnyard millet, buckwheat, or pulse. Since DNA is thermally stable and a trace amount of DNA can be detected even in processed foods, the allergen detection method according to the present invention provides data that can be used not only for food labeling and food allergen information but also for the detection of trace amounts of residual food additives (e.g. processing aids, carry-overs) and the detection of contaminants that are not intended by manufacturers (e.g., cross-contamination between the manufacturing lines).

In addition to these applications, the present invention is also applicable to parentage testing for mammals including human, the identification of the pedigree of livestock, the identification of varieties of agricultural products, SNP detection, the detection of diseases (e.g. cancer) caused by gene mutations, and other applications. More specifically, for example, in applications relating to livestock, the present invention can be used for pedigree registration, individual identification, parentage determination, removal of carrier individuals with virulence genes, and other applications. It should be noted that the present invention is not limited to the embodiments described and illustrated above and any modification may be made within the scope of the appended claims. Also, any appropriate combinations of technical means disclosed in the different embodiments are included in the technical scope of the present invention.

EXAMPLES

The present invention is described in more detail below with reference to examples. However, the technical scope of the present invention is not limited to these examples.

Example 1

(1) Synthesis of RNA as Template

In the present example, a synthetic RNA (miR-156a, chain length 20 mers) which was synthesized by Tsukuba Oligo Service Co., Ltd. was used as a template.

```
Template miR-156a:
                                    (SEQ ID No: 1)
5'-UGACAGAAGAGAGUGAGCAC-3'
```

(2) Synthesis of Reverse Transcription Primer

A reverse transcription primer RTp having on its 3'-end side a sequence complementary to six bases on the 3'-end side of the template miR-156a was synthesized. The primer was custom-synthesized by Tsukuba Oligo Service Co., Ltd.

```
RTp:
                                    (SEQ ID No: 2)
5'-GTTGGCTCTGGTGCAGGGTCCGAGGTATTCGCACCAGAGC
CAACGTGCTC-3'
```

Within the sequence of the primer, the sequence that hybridizes to the target nucleic acid is underlined.

(3) Reverse Transcription Reaction

A reverse transcription reaction was carried out using the template miR-156a synthesized in step (1) as a template and the reverse transcription primer synthesized in step (2), according to the protocol of PrimeScript (registered trademark) High Fidelity RT-PCR Kit (Takara Bio, Inc.).

A reverse transcription reaction mixture (20 µl) was prepared by adding the template miR-156a (1 fmol), the 10 µM reverse transcription primer RTp (2 µl), 5× PrimeScript Buffer (4 µl), 40 U/µl RNase Inhibitor (0.5 µl), 200 U/µl PrimeScript RTase (1.0 µl), and RNase-free water. Subsequently, a reverse transcription reaction was carried out under gentle mixing at 30° C. for 10 minutes, at 42° C. for 30 minutes, and at 95° C. for 5 minutes to produce a cDNA of miR-156a.

(4) Synthesis of Primer with Azobenzene and FITC-Modified Primer

A forward primer F having a sequence identical to the 5'-end side of the reverse transcription product produced in step (3) and a reverse primer R having a sequence complementary to the 3'-end side of the reverse transcription product were designed. Further, a tagged primer (T-X-R)

was prepared by incorporating a polymerase inhibitory region (X) having an azobenzene structure (non-nucleic acid) and a tag sequence T into the 5' end of the reverse primer R. Further, a labeled primer (H-F) was prepared by incorporating FITC into the 5' end of the forward primer F.

The primer set prepared in this experiment is as follows.

```
T-X-R:
                                        (SEQ ID No: 3)
5'--GGTTAGCTTCCAACCACGTGTATGATC-X-GCGGCGGTG
ACAGAAGAGAGT-3'

H-F:
                                        (SEQ ID No: 4)
5'--FITC-GTGCAGGGTCCGAGGT-3'
```

(5) PCR Using Primer with Azobenzene and FITC-Modified Primer

PCR was carried out using the reverse transcription product produced in step (3) as a template and the primer set prepared in step (4). A PCR reaction mixture (100 μl) was prepared by adding the primer T-X-R (15 pmol), the primer H-F (15 pmol), and the reverse transcription reaction solution obtained in step (3) (0.5 μl) to a 0.2-ml PCR tube, and following the instruction manual of an ExTaq PCR device (Takara Bio, Inc.). Subsequently, the tube was set in a thermal cycler (GeneAmp PCR System, Applied Biosystems) and subjected to heat treatment at 95° C. for 5 minutes and then exposed to 35 cycles of 95° C. for 30 seconds, 55° C. for 30 seconds, and 72° C. for 30 seconds. In this manner, a PCR amplification product was obtained. Further, PCR was performed on the non-reverse-transcribed RNA (miR-156a) (negative control 1) and a sample prepared by subjecting a separate mouse total RNA to the reverse transcription reaction in step (3) (negative control 2).

(6) Preparation of Anti-FITC Antibody-Bound Gold Colloid

Gold Colloid (40 nm, $9.0 \times 10^{10}$ (particles/ml), British BioCell International) and an anti-FITC antibody solution (5 mM phosphate buffer, pH 7) were mixed and left to stand for 20 minutes at room temperature. One half volume of a solution containing 1% BSA and 0.1% PEG was added, and the resulting mixture was centrifuged at 10000 rpm for 25 minutes. After removing the supernatant, the residue was mixed with the solution containing 1% BSA and 0.1% PEG, and the mixture was then centrifuged at 10000 rpm for 25 minutes. After centrifugation, the supernatant was removed, and 5 mM phosphate buffer (pH 7) was added. This buffer replacement procedure was repeated again. The gold colloid solution thus prepared was mixed with a surfactant and uniformly applied to a glass fiber pad, followed by drying in a vacuum oven. In this manner, a conjugate pad was prepared.

(7) Immobilization of Capture Oligonucleotide Probe on Solid Phase

A 3'-biotin-modified oligonucleotide probe having a sequence (SEQ ID NO:5) complementary to the tag region (SEQ ID NO:3) was mixed with streptavidin. The mixture was applied along a line on a nitrocellulose membrane (product name: Hi-Flow 180, Millipore) with a dispenser, and air-dried at 40° C. for 30 minutes.

```
Oligonucleotide probe 1:
                                        (SEQ ID No: 5)
5'-(GATCATACACGTGGTTGGAAGCTAACC)-Biotin-3'
```

(8) Preparation of Nucleic Acid Chromatographic Test Strip

A test strip for detecting the PCR amplification product obtained using the set of the azobenzene-inserted primer and the FITC-modified primer was prepared by bonding the following components to a substrate consisting of a backing sheet as shown in FIG. 6: a chromatographic medium consisting of the nitrocellulose membrane prepared above, the conjugate pad prepared above, a universal sample pad serving as a sample application zone, and an absorption pad for absorbing the developed samples and labeling substance.

(9) Detection of PCR Product Using Test Strip

The PCR products produced in step (5) were each immediately applied, without being denatured, to the sample application zone on the test strip prepared in step (8) for detection by chromatography. When the reverse transcribed target miR156a obtained in step (3) was used as a template, a colored line specific to the target nucleic acid was detected on the test line. In contrast, no line was detected for the PCR product obtained using the non-reverse-transcribed miR156a (negative control 1). Likewise, no line was detected for the PCR product obtained using the reverse transcription product of the mouse total RNA (negative control 2) as a template. The detection by chromatography took only 10 to 15 minutes.

Example 2

(1) Extraction of Total RNA from *Arabidopsis*

*Arabidopsis* (1 g) was ground in liquid nitrogen with a mortar. Subsequently, a simple RNA extraction kit (for RT-PCR) was used according to the protocol to extract total RNA.

(2) Poly(A) Addition

A poly(A) addition reaction was performed on the RNA extracted from *Arabidopsis* using a poly(A) polymerase (New England Biolabs). A total of 20 μl of a mixture was prepared by adding 10× buffer (2 μl), 10 mM ATP (2 μl), the extracted RNA (2 μl), the poly(A) polymerase (1 U), and RNase-free water. The mixture was reacted at 37° C. for 10 minutes to add a poly(A) sequence to the 3' end of the RNA.

(3) Synthesis of Reverse Transcription Primer

A reverse transcription primer RTp-T having on its 3'-end side a sequence complementary to the poly(A) portion on the 3'-end side of the RNA was synthesized. The primer was custom-synthesized by Tsukuba Oligo Service Co., Ltd. (V=A, G, or C; N=A, T, G, or C)

```
RTp-T:
                                        (SEQ ID No: 6)
5'-GTTGGCTCTGGTGCAGGGTCCGAGGTATTCGCACCAGAGCCAACTTT
TTTTTTTTTTTVN-3'
```

(4) Reverse Transcription Reaction

A reverse transcription reaction was carried out using the poly(A)-added RNA produced in step (2) as a template and the reverse transcription primer RTp-T synthesized in step (3) as a reverse transcription primer according to the protocol of PrimeScript (registered trademark) High Fidelity RT-PCR Kit (Takara Bio, Inc.).

A reverse transcription reaction mixture (20 μl) was prepared by adding the poly(A)-added RNA (1 μl), the 10 μM reverse transcription primer RTp-T (2 μl), 5× PrimeScript Buffer (4 μl), 40 U/μl RNase Inhibitor (0.5 μl), 200 U/μl PrimeScript RTase (1.0 μl), and RNase-free water. Subsequently, a reverse transcription reaction was carried out under gentle mixing at 30° C. for 10 minutes, at 42° C. for 30 minutes, and at 95° C. for 5 minutes to produce a cDNA of miR-156a.

(5) Synthesis of Primer with Aliphatic Chain and FITC-Modified Primer

A forward primer F having a sequence identical to the 5'-end side of the reverse transcription product produced in step (4) and a reverse primer R having a sequence complementary to the 3'-end side of the reverse transcription product were designed. Further, a tagged primer (T-X-R) was prepared by incorporating a polymerase inhibitory region (XS) having an aliphatic chain structure (non-nucleic acid) and a tag sequence T into the 5' end of the reverse primer R. Further, a labeled primer (H-F) was prepared by incorporating FITC into the 5' end of the forward primer F.

The primer set prepared in this experiment is as follows.

```
T-XS-R:
                                        (SEQ ID No: 7)
5'--GGTTAGCTTCCAACCACGTGTATGATC-XS-GCGGCGGTGACAGAA

GAGAGT-3'

H-F:
                                        (SEQ ID No: 8)
5'--FITC-GTGCAGGGTCCGAGGT-3'
```

(6) PCR Using Primer with Aliphatic Chain and FITC-Modified Primer

PCR was carried out using the reverse transcription product produced in step (4) as a template and the primer set prepared in step (5). A PCR reaction mixture (100 μl) was prepared by adding the primer T-X-R (15 pmol), the primer H-F (15 pmol), and the reverse transcription reaction solution obtained in step (4) (0.5 μl) to a 0.2-ml PCR tube, and following the instruction manual of an ExTaq PCR device (Takara Bio, Inc.). Subsequently, the tube was set in a thermal cycler (GeneAmp PCR System, Applied Biosystems) and subjected to heat treatment at 95° C. for 5 minutes and then exposed to 35 cycles of 95° C. for 30 seconds, 55° C. for 30 seconds, and 72° C. for 30 seconds. In this manner, a PCR amplification product was obtained. Further, PCR was performed on the non-reverse-transcribed RNA (miR-156a) (negative control 1) and a sample prepared by subjecting a separate mouse total RNA to the reverse transcription reaction in step (4) (negative control 2).

(7) Preparation of Anti-FITC Antibody-Bound Gold Colloid

Gold Colloid (40 nm, $9.0 \times 10^{10}$ (particles/ml), British BioCell International) and an anti-FITC antibody solution (5 mM phosphate buffer, pH 7) were mixed and left to stand for 20 minutes at room temperature. One half volume of a solution containing 1% BSA and 0.1% PEG was added, and the resulting mixture was centrifuged at 10000 rpm for 25 minutes. After removing the supernatant, the residue was mixed with the solution containing 1% BSA and 0.1% PEG, and the mixture was then centrifuged at 10000 rpm for 25 minutes. After centrifugation, the supernatant was removed, and 5 mM phosphate buffer (pH 7) was added. This buffer replacement procedure was repeated again. The gold colloid solution thus prepared was mixed with a surfactant and uniformly applied to a glass fiber pad, followed by drying in a vacuum oven. In this manner, a conjugate pad was prepared.

(8) Immobilization of Capture Oligonucleotide Probe on Solid Phase

An application solution of an oligonucleotide probe having a sequence (SEQ ID No:9) complementary to the tag region (SEQ ID No:7) was prepared. The application solution was applied along a line on a nitrocellulose membrane (product name: Hi-Flow 180, Millipore) with a dispenser, and air-dried at 40° C. for 30 minutes.

```
Oligonucleotide probe 2:
                                        (SEQ ID No: 9)
5'-(GATCATACACGTGGTTGGAAGCTAACC)-3'
```

(9) Preparation of Nucleic Acid Chromatographic Test Strip

A test strip for detecting the PCR amplification product obtained using the set of the aliphatic chain-inserted primer and the FITC-modified primer was prepared by bonding the following components to a substrate consisting of a backing sheet as shown in FIG. 6: a chromatographic medium consisting of the nitrocellulose membrane prepared above, the conjugate pad prepared above, a universal sample pad serving as a sample application zone, and an absorption pad for absorbing the developed samples and labeling substance.

(10) Detection of PCR Product Using Test Strip

The PCR products produced in step (6) were each mixed, without being denatured, with a developing solution containing a surfactant and sodium chloride and immediately applied to the sample application zone on the test strip prepared in step (9) for detection by chromatography. When the reverse transcribed target miR156a obtained in step (4) was used as a template, a colored line specific to the target nucleic acid was detected on the test line. In contrast, no line was detected for the PCR product obtained using the non-reverse-transcribed miR156a (negative control 1). Likewise, no line was detected for the PCR product obtained using the reverse transcription product of the mouse total RNA as a template (negative control 2). The detection by chromatography took only 10 to 15 minutes.

Example 3

(1) Synthesis of RNAs 1 to 3 as Templates

Synthetic RNAs 1 to 3 which were synthesized by Tsukuba Oligo Service Co., Ltd. were used as templates.

```
Template miRNA:
                                   (SEQ ID No: 10)
5'-UGACAGAAGAGAGUGAGCAC-3'

Template miRNA 2:
                                   (SEQ ID No: 11)
5'-UUUGGAUUGAAGGGAGCUCUA-3'

Template miRNA 3:
                                   (SEQ ID No: 12)
5'-UGAUUGAGCCGCGCCAAUAUC-3'
```

(2) Synthesis of Reverse Transcription Primers

The following reverse transcription primers were synthesized: a reverse transcription primer RTp 1 having on its 3'-end side a sequence complementary to 6 bases on the 3'-end side of the template miRNA 1; a reverse transcription primer RTp 2 having on its 3'-end side a sequence complementary to 6 bases on the 3'-end side of the template miRNA 2; and a reverse transcription primer RTp 3 having on its 3'-end side a sequence complementary to 6 bases on the 3'-end side of the template miRNA 3. These primers were custom-synthesized by Tsukuba Oligo Service Co., Ltd.

```
RTp1:
                                   (SEQ ID No: 13)
5'-TGGGCTGACCTAGAGGTCTTAACGTGCTC-3'

RTp2:
                                   (SEQ ID No: 14)
5'-CCGGAACAGACACCAGGTTTAACTAGAGC-3'

RTp3:
                                   (SEQ ID No: 15)
5'-ATACCGATGAGTGTGCTACCAACGATATT-3'
```

(3) Reverse Transcription Reaction

Reverse transcription reactions were carried out using the templates miRNA 1 to miRNA 3 synthesized in step (1) as templates and the reverse transcription primers RTp 1 to RTp 3 synthesized in step (2), according to the protocol of PrimeScript (R) High Fidelity RT-PCR Kit (Takara Bio, Inc.).

The following samples (i) to (v) were prepared.
(i) Template miRNA 1 (1 nM)
(ii) Template miRNA 2 (1 nM)
(iii) Template miRNA 3 (1 nM)
(iv) Templates miRNA 1, miRNA 2, and miRNA 3 (a mixture containing 1 nM each)
(v) No template Reverse transcription reaction mixtures (20 µl each) were prepared by adding the 10 µM reverse transcription primers RTp 1 to RTp 3 (2 µl each), 5× PrimeScript Buffer (4 µl), 40 U/µl RNase Inhibitor (0.5 µl), 200 U/µl PrimeScript RTase (1.0 µl), and RNase-free water to each of the samples (1 µl). Subsequently, reverse transcription reactions of the samples (i) to (v) were carried out under gentle mixing at 30° C. for 10 minutes, at 42° C. for 30 minutes, and at 95° C. for 5 minutes to produce cDNAs.

(4) Synthesis of Azobenzene-Inserted Primer

Three primer sets including a set of a forward primer (F1) and a reverse primer (R1), a set of a forward primer (F2) and a reverse primer (R2), and a set of a forward primer (F3) and a reverse primer (R3) were designed to allow for nucleic acid amplification reactions using as templates the reverse transcription products cDNA 1 to cDNA 3 from the miRNA 1 to miRNA 3. Tagged-primers T1-X-F1 and T2-X-R1, T3-X-F2 and T4-X-R2, and T5-X-F3 and T6-X-R3 were synthesized by incorporating into the 5' ends of the primers a polymerase reaction inhibitory region (X) containing azobenzene (a non-nucleic acid structure) and a tag sequence T1 or T2, a tag sequence T3 or T4, and a tag sequence T5 or T6, respectively. These six azobenzene-inserted primers were purchased as products custom-synthesized by Tsukuba Oligo Service Co., Ltd. The three primer sets prepared in this experiment are as follows.

```
Tag sequence T1:
                                   (SEQ ID No: 16)
5'-(TGGCAACATTTTTCACTGGGTTTATAG)-3'

Tag sequence T2:
                                   (SEQ ID No: 17)
5'-(GGTTAGCTTCCAACCACGTGTAGATCA)-3'

Primer T1-X-F1:
                                   (SEQ ID No: 18)
5'-(TGGCAACATTTTTCACTGGGTTTATAG X TGGGCTGACCTAGAGG
TCTT)-3'

Primer T2-X-R1:
                                   (SEQ ID No: 19)
5'-(GGTTAGCTTCCAACCACGTGTAGATCA X GCGGCGGTGACAGAAG
AGAGT)-3'

Tag sequence T3:
                                   (SEQ ID No: 20)
5'-(CGCATTGAGCAAGTGTACAGAGCAT)-3'

Tag sequence T4:
                                   (SEQ ID No: 21)
5'-(ATTATGCGTGGAGAAGCATATCATA)-3'

Primer T3-X-F2:
                                   (SEQ ID No: 22)
5'-(CGCATTGAGCAAGTGTACAGAGCAT X CCGGAACAGACACCAGGT
TT)-3'

Primer T4-X-R2:
                                   (SEQ ID No: 23)
5'-(ATTATGCGTGGAGAAGCATATCATA X CGGCGGTTTGGATTGAAG
GGA)-3'

Tag sequence T5:
                                   (SEQ ID No: 24)
5'-(AATTGCGCATGTCCATGTGTAA)-3'

Tag sequence T6:
                                   (SEQ ID No: 25)
5'-(TACTTTAGAGGAAACTGCTGAG)-3'

Primer T5-X-F3:
                                   (SEQ ID No: 26)
5'-(AATTGCGCATGTCCATGTGTAA X ATACCGATGAGTGTGCTAC
C)-3'

Primer T6-X-R3:
                                   (SEQ ID No: 27)
5'-(TACTTTAGAGGAAACTGCTGAG X TTCCTTGATTGAGCCGCGC
C)-3'
```

(5) PCR Using Three Azobenzene-Inserted Primer Sets

PCR was carried out using the three primer sets prepared in step (4). PCR reaction mixtures (100 µl each) were prepared by adding the primer T1-X-F1, the primer T2-X-R1, the primer T3-X-F2, the primer T4-X-R2, the primer T5-X-F3, and the primer T6-X-R3 (15 pmol each), and each of the reverse transcription reaction solutions of the samples (i) to (v) produced in step (3) (1 μl) to a PCR tube, and following the instruction manual of an ExTaq PCR device (Takara Bio, Inc.).

After preparation of these reaction mixtures, the tubes were set in a thermal cycler (GeneAmp PCR System, Applied Biosystems) and subjected to heat treatment at 95° C. for 5 minutes and then exposed to 30 cycles of 95° C. for 30 seconds, 55° C. for 30 seconds, and 72° C. for 30 seconds. In this manner, amplified DNA fragments having the target sequences were obtained from the samples (i) to (iv). No amplified DNA fragments were obtained from the sample (v) (which was used as a negative control).

(6) Preparation of Latex-Bound Oligonucleotide Probe

A combination of a carboxyl group-containing polystyrene latex (blue) (solids content 10% (w/w), Bangs Laboratories, Inc.) and an amino group-containing oligonucleotide probe 3 (SEQ ID No:28, a strand complementary to SEQ ID No:16), a combination of a carboxyl group-containing polystyrene latex (orange) (solids content 10% (w/w), Bangs Laboratories, Inc.) and an amino group-containing oligonucleotide probe 4 (SEQ ID No:29, a strand complementary to SEQ ID No:20), or a combination of a carboxyl group-containing polystyrene latex (green) (solids content 10% (w/w), Bangs Laboratories, Inc.) and an amino group-containing oligonucleotide probe 5 (SEQ ID No:30, a strand complementary to SEQ ID No:24) was mixed and bonded to each other in MES buffer containing a necessary amount of a water-soluble carbodiimide, followed by blocking with monoethanolamine. These reaction solutions were centrifuged and the supernatants were then removed. The resulting precipitates were washed with water. After washing, each precipitate was resuspended in HEPES buffer containing a surfactant to prepare an oligonucleotide probe 3-bound latex (blue), oligonucleotide probe 4-bound latex (orange), and oligonucleotide probe 5-bound latex (green).

These three types of latex were uniformly applied to a glass fiber pad and then dried in a vacuum oven. In this manner, a conjugate pad was prepared.

```
Oligonucleotide probe 3:
                                        (SEQ ID No: 28)
5'-(CTATAAACCCAGTGAAAAATGTTGCCA)-NH2-3'

Oligonucleotide probe 4:
                                        (SEQ ID No: 29)
5'-(TTGCTCTGTACACTTGCTCAATGCG)-NH2-3'

Oligonucleotide probe 5:
                                        (SEQ ID No: 30)
5'-(TTACACATGGACATGCGCAATT)-NH2-3'
```

(7) Immobilization of Three Oligonucleotide Probes on Solid Phase

A 3'-biotin-modified oligonucleotide probe 6 having a sequence (SEQ ID NO:31) complementary to SEQ ID NO:17, a 3'-biotin-modified oligonucleotide probe 7 having a sequence (SEQ ID NO:32) complementary to SEQ ID NO:21, and a 3'-biotin-modified oligonucleotide probe 8 having a sequence (SEQ ID NO:33) complementary to SEQ ID NO:25 were each mixed with streptavidin. The mixtures were applied with dispensers to a nitrocellulose membrane (product name: Hi-Flow 135, Millipore) along three lines separated from one another, respectively, from the upstream side and then air-dried at 40° C. for 30 minutes. Three detection lines were formed.

```
Oligonucleotide probe 6:
                                        (SEQ ID No: 31)
5'-(GATCATACACGTGGTTGGAAGCTAACC)-Biotin-3'

Oligonucleotide probe 7:
                                        (SEQ ID No: 32)
5'-(TATGATATGCTTCTCCACGCATAAT)-Biotin-3'

Oligonucleotide probe 8:
                                        (SEQ ID No: 33)
5'-(CTCAGCAGTTTCCTCTAAAGTA)-Biotin-3'
```

(8) Preparation of Nucleic Acid Chromatographic Test Strip

A test strip for detecting the PCR amplification products obtained using the azobenzene-inserted primer sets was prepared by bonding the following components to a substrate consisting of a backing sheet as shown in FIG. 6: a chromatographic medium consisting of the nitrocellulose membrane prepared above, the conjugate pad prepared in step (6), a universal sample pad serving as a sample application zone, and an absorption pad for absorbing the developed samples and labeling substances.

(9) Detection of PCR Products Using Test Strip

The PCR products produced from the samples (i) to (v) in step (4) were each immediately applied, without being denatured, to the sample application zone on the test strip prepared in step (5) for detection by chromatography. The results are described below.

Sample (i): Only the first detection line was colored blue.
Sample (ii): Only the second detection line was colored orange.
Sample (iii): Only the third detection line was colored green.
Sample (iv): The first detection line was colored blue, the second detection line was colored orange, and the third detection line was colored green.
Sample (v): No color change was observed for any of the detection lines.

The results demonstrated that the analytes can be detected in a target gene-specific manner and that three analytes can be detected simultaneously. Further, the detection by chromatography took only 10 to 15 minutes.

Example 4

(1) Synthesis of RNAs 1 to 3 as Templates

Synthetic RNAs 1 to 3 which were synthesized by Tsukuba Oligo Service Co., Ltd. were used as templates.

```
Template miRNA:
                                        (SEQ ID No: 34)
5'-UGACAGAAGAGAGUGAGCAC-3'

Template miRNA 2:
                                        (SEQ ID No: 35)
5'-UUUGGAUUGAAGGGAGCUCUA-3'
```

Template miRNA 3:

(SEQ ID No: 36)
5'-UGAUUGAGCCGCGCCAAUAUC-3'

(2) Poly(A) Addition

A poly(A) addition reaction was performed on the templates miRNA 1 to miRNA 3 using a poly(A) polymerase (New England Biolabs).
The following samples (i) to (v) were prepared.
(i) Template miRNA 1 (1 nM)
(ii) Template miRNA 2 (1 nM)
(iii) Template miRNA 3 (1 nM)
(iv) Templates miRNA 1, miRNA 2, and miRNA 3 (a mixture containing 1 nM each)
(v) No template Mixtures (20 μl each) were prepared by adding each of the samples (i) to (v) (1 μl), 10× buffer (2 μl), 10 mM ATP (2 μl), the extracted RNA (2 μl), the poly(A) polymerase (1 U), and RNase-free water. These mixtures were reacted at 37° C. for 10 minutes to add a poly(A) sequence to the 3' end of each miRNA.

(3) Synthesis of Reverse Transcription Primer

A reverse transcription primer RTp-T having on its 3'-end side a sequence complementary to the poly(A) portion on the 3'-end side of each template miRNA was synthesized. The primer was custom-synthesized by Tsukuba Oligo Service Co., Ltd. (V=A, G, or C, N=A, T, G, or C)

RTp-T:

(SEQ ID No: 37)
5'-GTTGGCTCTGGTGCAGGGTCCGAGGTATTCGCACCAGAGCCAAC<u>TTT
TTTTTTTTTTTVN</u>-3'

(4) Reverse Transcription Reaction

Reverse transcription reactions were carried out using the poly(A)-added samples produced in step (2) as templates and the reverse transcription primer RTp-T synthesized in step (3), according to the protocol of PrimeScript (registered trademark) High Fidelity RT-PCR Kit (Takara Bio, Inc.).

Reverse transcription reaction mixtures (20 μl each) were prepared by adding each of the poly(A) addition reaction solutions of the samples (i) to (v) (1 μl), the 10 μM reverse transcription primer RTp-T (2 μl), 5× PrimeScript Buffer (4 μl), 40 U/μl RNase Inhibitor (0.5 μl), 200 U/μl PrimeScript RTase (1.0 μl), and RNase-free water. Subsequently, reverse transcription reactions were carried out under gentle mixing at 30° C. for 10 minutes, at 42° C. for 30 minutes, and at 95° C. for 5 minutes to produce reverse transcription products of the samples.

(5) Synthesis of Azobenzene-Inserted Primer and Biotin-Modified Primer

A forward primer (F) and reverse primers (R1) to (R3) were designed to allow for nucleic acid amplification reactions using as templates the reverse transcription products cDNA 1 to cDNA 3 from the miRNA 1 to miRNA 3 to which a poly(A) sequence had been added. B-F was synthesized by incorporating a biotin modification into the 5' end of the forward primer. Tagged-primers T7-X-R1, T8-X-R2, and T9-X-R3 were synthesized by incorporating into each of the reverse primers (R1) to (R3) a sequence complementary to the 3'-end side of the reverse transcription products cDNA 1 to cDNA 3, respectively, and also incorporating into each 5'-end side a polymerase reaction inhibitory region (X) containing azobenzene (a non-nucleic acid structure) and tag sequences T7, T8, and T9, respectively. These four modified primers were purchased as products custom-synthesized by Tsukuba Oligo Service Co., Ltd. The three primer sets prepared in this experiment are as follows.

B-F:

(SEQ ID No: 38)
5'--Biotin-TCTGGTGCAGGGTCCGAGGTA-3'

Tag sequence T7:

(SEQ ID No: 39)
5'-(GGTTAGCTTCCAACCACGTGTAGATCA)-3'

Primer T7-X-R1:

(SEQ ID No: 40)
5'-(GGTTAGCTTCCAACCACGTGTAGATCA X GCGGCGGTGACAGAAG AGAGT)-3'

Tag sequence T8:

(SEQ ID No: 41)
5'-(ATTATGCGTGGAGAAGCATATCATA)-3'

Primer T8-X-R2:

(SEQ ID No: 42)
5'-(ATTATGCGTGGAGAAGCATATCATA X CGGCGGTTTGGATTGAAG GGA)-3'

Tag sequence T9:

(SEQ ID No: 43)
5'-(TACTTTAGAGGAAACTGCTGAG)-3'

Primer T9-X-R3:

(SEQ ID No: 44)
5'-(TACTTTAGAGGAAACTGCTGAG X TTCCTTGATTGAGCCGCGC C)-3'

(6) PCR Using Set of Azobenzene-Inserted Primer and Biotin Primer

PCR was carried out using the primer sets prepared in step (5). PCR reaction mixtures (100 μl each) were prepared by adding the primer H-F, the primer T7-X-R1, the primer T8-X-R2, and the primer T9-X-R3 (15 pmol each), and each of the reverse transcription reaction solutions of the samples (i) to (v) obtained in step (4) (1 μl) to a PCR tube, and following the instruction manual of an ExTaq PCR device (Takara Bio, Inc.).

After preparation of these reaction mixtures, the tubes were set in a thermal cycler (GeneAmp PCR System, Applied Biosystems) and subjected to heat treatment at 95° C. for 5 minutes and then exposed to 30 cycles of 95° C. for 30 seconds, 55° C. for 30 seconds, and 72° C. for 30 seconds. In this manner, amplified DNA fragments having the target sequences were obtained from the samples (i) to (iv). No amplified DNA fragments were obtained from the sample (v) (which was used as a negative control).

(7) Preparation of Streptavidin-Bound Gold Colloid

Gold Colloid (40 nm, $9.0 \times 10^{10}$ (particles/ml), British BioCell International) and a streptavidin solution (5 mM phosphate buffer, pH 7) were mixed and left to stand for 20 minutes at room temperature. One half volume of a solution containing 1% BSA and 0.1% PEG was added, and the resulting mixture was centrifuged at 10000 rpm for 25 minutes. After removing the supernatant, the residue was mixed with the solution containing 1% BSA and 0.1% PEG, and the mixture was then centrifuged at 10000 rpm for 25 minutes. After centrifugation, the supernatant was removed, and 5 mM phosphate buffer (pH 7) was added. This buffer replacement procedure was repeated again. The gold colloid solution thus prepared was mixed with a surfactant and uniformly applied to a glass fiber pad, followed by drying in a vacuum oven. In this manner, a conjugate pad was prepared.

(8) Immobilization of Three Oligonucleotide Probes on Solid Phase

An application solution of an oligonucleotide probe 9 having a sequence (SEQ ID No:45) complementary to SEQ ID No:39, an application solution of an oligonucleotide probe 10 having a sequence (SEQ ID No:46) complementary to SEQ ID No:41, and an application solution of an oligonucleotide probe 11 having a sequence (SEQ ID No:47) complementary to SEQ ID No:43 were prepared. These application solutions were applied with dispensers to a nitrocellulose membrane (product name: FF170HP, Whatman) along three lines separated from one another, respectively, from the upstream side and then air-dried at 40° C. for 30 minutes. In this manner, three detection lines were formed.

```
Oligonucleotide probe 9:
                                         (SEQ ID No:45)
5'-(GATCTACACGTGGTTGGAAGCTAACC)-3'

Oligonucleotide probe 10:
                                         (SEQ ID No:46)
5'-(TATGATATGCTTCTCCACGCATAAT)-3'

Oligonucleotide probe 11:
                                         (SEQ ID No:47)
5'-(CTCAGCAGTTTCCTCTAAAGTA)-3'
```

(9) Preparation of Nucleic Acid Chromatographic Test Strip

A test strip for detecting the PCR amplification products obtained using the azobenzene-inserted primer sets was prepared by bonding the following components to a substrate consisting of a backing sheet as shown in FIG. 6: a chromatographic medium consisting of the nitrocellulose membrane prepared in step (8), the conjugate pad prepared in step (7), a universal sample pad serving as a sample application zone, and an absorption pad for absorbing the developed samples and labeling substance.

(10) Detection of PCR Products Using Test Strip

The PCR products of the samples (i) to (v) prepared in step (4) were each immediately applied, without being denatured, to the sample application zone on the test strip prepared in step (9) for detection by chromatography. The results are described below.
Sample (i): Only the first detection line was colored.
Sample (ii): Only the second detection line was colored.
Sample (iii): Only the third detection line was colored.
Sample (iv): The first, second, and third detection lines were all colored.
Sample (v): No color change was observed for any of the detection lines.

Figure 10:
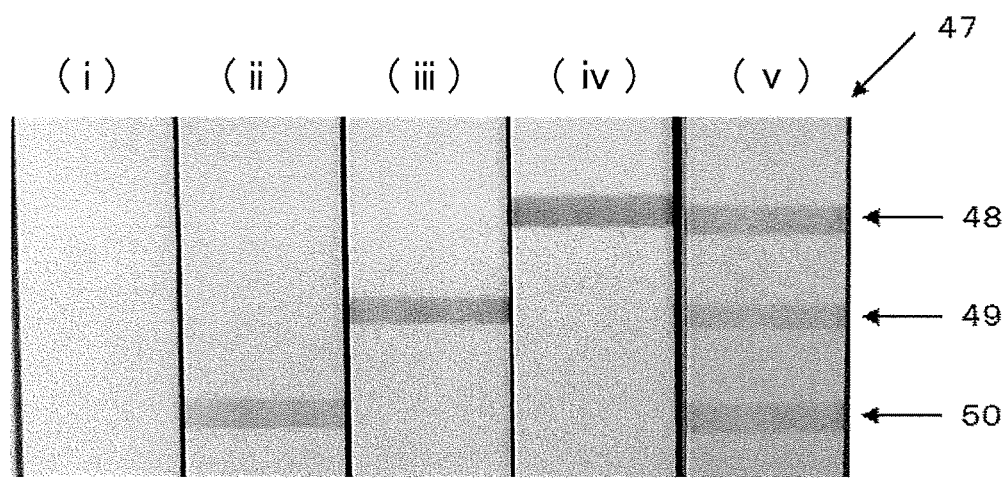
FIG. 10 shows part of the results of detection of PCR amplification products using a nucleic acid chromatographic strip in Example 4.

The results demonstrated that the analytes can be detected in a target gene-specific manner and that three analytes can be detected simultaneously. FIG. 10 shows the results. Further, the detection by chromatography took only 10 to 15 minutes.

Example 5

(1) Synthesis of RNA as Template

A template miR-156a was synthesized as in Example 1.

(2) Synthesis of Reverse Transcription Primer

A reverse transcription primer RTp was synthesized as in Example 1.

(3) Reverse Transcription Reaction

A reverse transcription reaction was carried out using the template miR-156a synthesized in step (1) as a template and the reverse transcription primer synthesized in step (2), according to the protocol of PrimeScript (registered trademark) High Fidelity RT-PCR Kit (Takara Bio, Inc.).

The following samples having different template concentrations were prepared.
(i) No template
(ii) Template miR-156a 1 pM
(iii) Template miR-156a 10 pM
(iv) Template miR-156a 100 pM The samples (i) to (iv) (2 µl each) were added to respective tubes and reverse transcribed under the same conditions as in step (3) of Example 1. A cDNA of miR-156a was produced from each sample.

(4) Synthesis of Polymerase Reaction Inhibitory Region (5'-5' Linkage+3'-3' Linkage)-Inserted Primer and DIG-Modified Primer A forward primer F having a sequence identical to the 5'-end side of the reverse transcription product produced in step (3) and a reverse primer R having a sequence complementary to the 3'-end side of the reverse transcription product were designed. Further, a tagged primer (T-X-R) was prepared by incorporating a polymerase inhibitory region (Xr) having a 5'-5' linkage+3'-3' linkage structure and a tag sequence T into the 5' end of the reverse primer R. Further, a labeled primer (D-F) was prepared by incorporating DIG into the 5' end of the forward primer F.

The primer set prepared in this experiment is as follows.

```
T-Xr-R:
                                         (SEQ ID No: 48)
5'--GGTTAGCTTCCAACCACGTGTATGATC-Xr-GCGGCGGTGACAGAA
GAGAGT-3'

D-F:
                                         (SEQ ID No: 49)
5'--DIG-GTGCAGGGTCCGAGGT-3'
```

(5) PCR Using Polymerase Reaction Inhibitory Region (5'-5' Linkage+3'-3' Linkage)-Inserted Primer and DIG-Modified Primer PCR was carried out on each sample using the reverse transcription product produced in step (3) as a template and the primer set prepared in step (4). PCR reaction mixtures (100 µl each) were prepared by adding the primer T-Xr-R (15 pmol), the primer D-F (15 pmol), and each of the reverse transcription reaction solutions (0.5 µl) obtained in step (3) to a 0.2-ml PCR tube, and following the instruction manual of an ExTaq PCR kit (Takara Bio, Inc.). Subsequently, the tubes were set in a thermal cycler (GeneAmp PCR System, Applied Biosystems) and subjected to heat treatment at 95° C. for 5 minutes and then exposed to 30 cycles of 95° C. for 30 seconds, 55° C. for 30 seconds, and 72° C. for 30 seconds. In this manner, PCR amplification products were obtained.

(6) Preparation of Anti-DIG Antibody-Bound Gold Colloid

Gold Colloid (40 nm, $9.0 \times 10^{10}$ (particles/ml), British BioCell International) and an anti-DIG antibody solution (5 mM phosphate buffer, pH 7) were mixed and left to stand for 20 minutes at room temperature. One half volume of a solution containing 1% BSA and 0.1% PEG was added, and the resulting mixture was centrifuged at 10000 rpm for 25 minutes. After removing the supernatant, the residue was mixed with the solution containing 1% BSA and 0.1% PEG, and the mixture was then centrifuged at 10000 rpm for 25 minutes. After centrifugation, the supernatant was removed, and 5 mM phosphate buffer (pH 7) was added. This buffer replacement procedure was repeated again. The gold colloid solution thus prepared was mixed with a surfactant and uniformly applied to a glass fiber pad, followed by drying in a vacuum oven. In this manner, a conjugate pad was prepared.

(7) Immobilization of Capture Oligonucleotide Probe on Solid Phase

A 3'-biotin-modified oligonucleotide probe having a sequence (SEQ ID NO:5) complementary to the tag region (SEQ ID NO:3) was mixed with streptavidin. The mixture was applied along a line on a nitrocellulose membrane (product name: Hi-Flow 180, Millipore) with a dispenser, and air-dried at 40° C. for 30 minutes.

```
Oligonucleotide probe 12:
                                       (SEQ ID No: 50)
5'-(GATCATACACGTGGTTGGAAGCTAACC)-Biotin-3'
```

(8) Preparation of Nucleic Acid Chromatographic Test Strip

A test strip for detecting the PCR amplification product obtained using the set of the 5'-5' linkage+3'-3' linkage-inserted primer and the DIG-modified primer was prepared by bonding the following components to a substrate consisting of a backing sheet as shown in FIG. 6: a chromatographic medium consisting of the nitrocellulose membrane prepared above, the conjugate pad prepared above, a universal sample pad serving as a sample application zone, and an absorption pad for absorbing the developed samples and labeling substance.

(9) Detection of PCR Products Using Test Strip

The PCR products produced in step (5) were each immediately applied, without being denatured, to the sample application zone on the test strip prepared in step (8) for detection by chromatography. When the reverse transcription products produced from the samples (ii) to (iv) by a reverse transcription reaction in step (3) were used as templates, a colored line specific to the target nucleic acid was detected on the test line in each case. In contrast, when the reverse transcription reaction solution of the sample (i) was used as a template, no line was detected. The detection by chromatography took only 10 to 15 minutes. In addition, the color intensity of each line was measured with a chromatoreader (Hamamatsu Photonics K.K.) and found to correlate with the concentration of the target RNA (miRNA 156) in the samples (i) to (iv), and the color differences between the lines were visually observable. The color intensities of the samples detected on the test line are as follows.

Sample (i): 2 mABS
Sample (ii): 114 mABS
Sample (iii): 153 mABS
Sample (iv): 173 mABS

REFERENCE SIGNS LIST

1. Target RNA
2. Reverse transcription primer
3. Primer body region with a sequence complementary to a portion of target RNA
4. Additional sequence not derived from target sequence
5. Reverse transcription product cDNA
6. Target RNA (having a poly(A) sequence at the 3' end)
7. Reverse transcription primer
8. Primer body region having a poly(T) sequence
9. Any additional sequence not derived from target sequence
10. Reverse transcription product cDNA (having a poly(T) sequence)
11. Primer body region
12. Tag region
13. Polymerase reaction inhibitory region
14. Reverse primer
15. Primer body region of reverse primer
16. Polymerase reaction inhibitory region
17. Tag region
18. Forward primer
19. Primer body region having a sequence identical to a 5'-end portion of reverse transcription product
20. Polymerase reaction inhibitory region
21. Tag region
22. Amplified DNA product having a single-stranded region at each end
23. Reverse primer
24. Primer body region of reverse primer
25. Polymerase reaction inhibitory region
26. Tag region
27. Forward primer
28. Primer body region having a sequence identical to a 5'-end portion of reverse transcription product
29. Labeling substance-binding region
30. Amplified DNA product having a single-stranded region at an end and a labeling substance-binding region at the other end
31. Sample pad
32. Conjugate pad
33. Carrier carrying capture oligonucleotide
34. Absorption pad 35. Substrate
36. Test line
37. Control line
38. Substance capable of specifically binding to labeling substance-binding region
39. Colored carrier (labeling molecule)
40. First complex of labeling molecule and amplified DNA product
41. Porous membrane
42. Capture oligonucleotide
43. Oligonucleotide labeled with labeling molecule
44. Labeling molecule
45. Carrier (microarray) with wells each carrying capture oligonucleotide
46. Bead carrier carrying capture oligonucleotide
47. Nitrocellulose membrane of chromatographic strip (only detection portion is shown)
48. Test line 1
49. Test line 2
50. Test line 3

The invention claimed is:

1. A micro RNA detection method, comprising the following steps (a) to (d):
   (a) adding a poly(A) sequence of three or more bases to a target micro RNA;
   (b) carrying out a reverse transcription reaction using the target micro RNA as a template and a reverse transcription primer having, on its 5'-end side, a sequence non-complementary to the target micro RNA to produce a reverse transcription product longer than the target micro RNA;
   (c) carrying out a nucleic acid amplification reaction using the reverse transcription product as a template and two primers, wherein at least one of the primers contains a polymerase reaction inhibitory region, to produce an amplified double-stranded DNA fragment having a single-stranded region at least at one end; and
   (d) hybridizing the single-stranded region of the amplified double-stranded DNA fragment to an oligonucleotide probe immobilized on a solid phase,
   wherein one of the two primers used in step (c) comprises
   a region comprising a nucleotide sequence that is complementary to the nucleotide sequence of the 3'-end of the reverse transcription product, and
   a tag region comprising a nucleotide sequence that is complementary to the oligonucleotide probe immobilized on the solid phase.

2. The nucleic acid detection method according to claim 1, wherein the target micro RNA has a base sequence of 10 or more bases.

3. The nucleic acid detection method according to claim 1 or 2, wherein the target micro RNA has a base sequence of 15 or more bases.

4. The nucleic acid detection method according to claim 1, wherein the reverse transcription primer contains a sequence of three or more bases complementary to the target micro RNA.

5. The nucleic acid detection method according to claim 1, wherein the reverse transcription primer contains a poly (T) sequence of three or more bases.

6. The nucleic acid detection method according to claim 5, wherein the reverse transcription primer contains on its 3'-end side a sequence of one or more bases complementary to the target micro RNA.

7. The nucleic acid detection method according to claim 1, wherein the reverse transcription product is longer than the target micro RNA by three or more bases.

8. The nucleic acid detection method according to claim 1, wherein the sequence non-complementary to the target micro RNA is a sequence containing therein mutually complementary sequences of five or more bases so as to be able to form a loop structure.

9. The nucleic acid detection method according to claim 1, wherein both of the primers of step (c) contain a tag region, a polymerase reaction inhibitory region, and a region having a sequence capable of hybridizing to the reverse transcription product or its complementary strand.

10. The nucleic acid detection method according to claim 9,
wherein the polymerase reaction inhibitory region contains a nucleic acid derivative.

11. The nucleic acid detection method according to claim 10,
wherein the nucleic acid derivative is at least one selected from the group consisting of an L-nucleic acid, a 3-deoxy-2-hydroxy-dN, a nucleic acid containing a modified base, a nucleic acid containing a damaged base, a nucleic acid containing a modified phosphate linkage, an RNA, a 2'-OMe-N, and derivatives thereof.

12. The nucleic acid detection method according to claim 10,
wherein the nucleic acid derivative is linked via a 5'-5' linkage to the region having a sequence capable of hybridizing to the reverse transcription product or its complementary strand and/or linked to the tag region via a 3'-3' linkage.

13. The nucleic acid detection method according to claim 9,
wherein the polymerase reaction inhibitory region contains a non-nucleic acid derivative.

14. The nucleic acid detection method according to claim 13,
wherein the non-nucleic acid derivative has a D-threoninol scaffold.

15. The nucleic acid detection method according to claim 14,
wherein the D-threoninol scaffold incorporates at least one selected from the group consisting of azobenzene, biotin, EDTA, and a chromophore.

16. The nucleic acid detection method according to claim 13,
wherein the non-nucleic acid derivative is at least one selected from the group consisting of a carbon chain ($C_n$), a PEG chain (($CH_2CH_2O)_n$), a disulfide-containing chain ($C_nSSC_n$), dithiol phosphoramidite, and derivatives thereof.

17. The nucleic acid detection method according to any one of claims 11 to 16,
wherein the primers contain multiple types of polymerase reaction inhibitory regions and/or contains a plurality of polymerase reaction inhibitory regions.

18. The nucleic acid detection method according to claim 9,
wherein the tag region has a nucleic acid sequence in the same orientation as the region having a sequence capable of hybridizing to the reverse transcription product or its complementary strand.

19. The nucleic acid detection method according to claim 9,
wherein the tag region contains a nucleic acid sequence in the same orientation as the region having a sequence capable of hybridizing to the reverse transcription product or its complementary strand, and a nucleic acid sequence in the opposite direction.

20. The nucleic acid detection method according to claim 1,
wherein the amplified double-stranded DNA fragment is capable of binding to a labeling substance.

21. The nucleic acid detection method according to claim 20,
wherein the amplified double-stranded DNA fragment is capable of binding to a labeling substance via the single-stranded region.

22. The nucleic acid detection method according to claim 20,
wherein the amplified double-stranded DNA fragment is capable of binding to a labeling substance via a sequence containing a labeling substance-binding substance.

23. The nucleic acid detection method according to claim 1, the method further comprising the step of binding the single-stranded region of the amplified double-stranded DNA fragment to a labeling substance.

24. The nucleic acid detection method according to any one of claims 20 to 23,
wherein the labeling substance comprises a colored carrier and allows for visual detection of the amplified double-stranded DNA fragment.

25. The nucleic acid detection method according to claim 1,
wherein the step of hybridizing the single-stranded region of the amplified double-stranded DNA fragment to an oligonucleotide probe immobilized on a solid phase is carried out on a nucleic acid detection device.

26. The nucleic acid detection method according to claim 25,
wherein the nucleic acid detection device is a chromatography device.

27. The nucleic acid detection method according to claim 25 or 26, the method comprising the following steps (a) to (c):
(a) placing the amplified double-stranded DNA fragment in a zone on the nucleic acid detection device which is different from a zone where the oligonucleotide probe is immobilized;
(b) diffusing the amplified double-stranded DNA fragment on the device with a solvent toward the zone where the oligonucleotide probe is immobilized; and
(c) hybridizing the amplified double-stranded DNA fragment to the oligonucleotide probe in the zone where the oligonucleotide probe is immobilized.

28. The nucleic acid detection method according to claim 27, the method further comprising before step (c) the step of binding the amplified double-stranded DNA fragment to the labeling substance.

29. The nucleic acid detection method according to claim 27, the method comprising the following steps (d) to (h):
(d) placing the amplified double-stranded DNA fragment and the labeling substance in respective zones on the nucleic acid detection device which are different from the zone where the oligonucleotide probe is immobilized;
(e) diffusing the amplified double-stranded DNA fragment with a solvent toward the zone where the labeling substance is placed;
(f) binding the amplified double-stranded DNA fragment to the labeling substance in the zone where the labeling substance is placed;
(g) diffusing a complex formed by binding in step (f) on the device toward the zone where the oligonucleotide probe is placed; and
(h) hybridizing the complex to the oligonucleotide probe in the zone where the oligonucleotide probe is immobilized.

* * * * *

SEQUENCE LISTING

```
<160> NUMBER OF SEQ ID NOS: 50

<210> SEQ ID NO 1
<211> LENGTH: 20
<212> TYPE: RNA
<213> ORGANISM: Artificial Sequence
<220> FEATURE:
<223> OTHER INFORMATION: Synthetic oligonucleotide:  template miR-156a

<400> SEQUENCE: 1
ugacagaaga gagugagcac                                              20

<210> SEQ ID NO 2
<211> LENGTH: 50
<212> TYPE: DNA
<213> ORGANISM: Artificial Sequence
<220> FEATURE:
<223> OTHER INFORMATION: Synthetic primer:  RTp

<400> SEQUENCE: 2
gttggctctg gtgcagggtc cgaggtattc gcaccagagc caacgtgctc              50

<210> SEQ ID NO 3
<211> LENGTH: 48
<212> TYPE: DNA
<213> ORGANISM: Artificial Sequence
<220> FEATURE:
<223> OTHER INFORMATION: Synthetic primer:  T-X-R
<220> FEATURE:
<221> NAME/KEY: misc_feature
<222> LOCATION: (27)..(28)
<223> OTHER INFORMATION: c at position 27 is joined to g at position 28
      by azobenzene represented by Formula (1) of the specification.

<400> SEQUENCE: 3
ggttagcttc caaccacgtg tatgatcgcg gcggtgacag aagagagt                48

<210> SEQ ID NO 4
<211> LENGTH: 16
<212> TYPE: DNA
<213> ORGANISM: Artificial Sequence
<220> FEATURE:
<223> OTHER INFORMATION: Synthetic primer:  H-F
<220> FEATURE:
<221> NAME/KEY: misc_feature
<222> LOCATION: (1)..(1)
<223> OTHER INFORMATION: modified with FITC.

<400> SEQUENCE: 4
gtgcagggtc cgaggt                                                   16

<210> SEQ ID NO 5
<211> LENGTH: 27
<212> TYPE: DNA
<213> ORGANISM: Artificial Sequence
<220> FEATURE:
<223> OTHER INFORMATION: Synthetic oligonucleotide: probe 1
```

```
<220> FEATURE:
<221> NAME/KEY: misc_feature
<222> LOCATION: (27)..(27)
<223> OTHER INFORMATION: modified with biotin.

<400> SEQUENCE: 5
gatcatacac gtggttggaa gctaacc                                              27

<210> SEQ ID NO 6
<211> LENGTH: 61
<212> TYPE: DNA
<213> ORGANISM: Artificial Sequence
<220> FEATURE:
<223> OTHER INFORMATION: Synthetic primer:  RTp-T
<220> FEATURE:
<221> NAME/KEY: misc_feature
<222> LOCATION: (61)..(61)
<223> OTHER INFORMATION: n is a, c, g, or t

<400> SEQUENCE: 6
gttggctctg gtgcagggtc cgaggtattc gcaccagagc caactttttt ttttttttv       60 n                                                                         61

<210> SEQ ID NO 7
<211> LENGTH: 48
<212> TYPE: DNA
<213> ORGANISM: Artificial Sequence
<220> FEATURE:
<223> OTHER INFORMATION: Synthetic primer:  T-X-R
<220> FEATURE:
<221> NAME/KEY: misc_feature
<222> LOCATION: (27)..(28)
<223> OTHER INFORMATION: c at position 27 is joined to g at position 28
      by C3 linker represented by Formula (6) of the specification.

<400> SEQUENCE: 7
ggttagcttc caaccacgtg tatgatcgcg gcggtgacag aagagagt                  48

<210> SEQ ID NO 8
<211> LENGTH: 16
<212> TYPE: DNA
<213> ORGANISM: Artificial Sequence
<220> FEATURE:
<223> OTHER INFORMATION: Synthetic primer:  H-F
<220> FEATURE:
<221> NAME/KEY: misc_feature
<222> LOCATION: (1)..(1)
<223> OTHER INFORMATION: modified with FITC.

<400> SEQUENCE: 8
gtgcagggtc cgaggt                                                          16

<210> SEQ ID NO 9
<211> LENGTH: 27
<212> TYPE: DNA
<213> ORGANISM: Artificial Sequence
<220> FEATURE:
<223> OTHER INFORMATION: Synthetic oligonucleotide: probe 2

<400> SEQUENCE: 9
gatcatacac gtggttggaa gctaacc                                              27

<210> SEQ ID NO 10
<211> LENGTH: 20
<212> TYPE: RNA
<213> ORGANISM: Artificial Sequence
<220> FEATURE:
<223> OTHER INFORMATION: Synthetic oligonucleotide:  template miRNA1
```

```
<400> SEQUENCE: 10
ugacagaaga gagugagcac                                                       20

<210> SEQ ID NO 11
<211> LENGTH: 21
<212> TYPE: RNA
<213> ORGANISM: Artificial Sequence
<220> FEATURE:
<223> OTHER INFORMATION: Synthetic oligonucleotide: template miRNA2

<400> SEQUENCE: 11
uuuggauuga agggagcucu a                                                     21

<210> SEQ ID NO 12
<211> LENGTH: 21
<212> TYPE: RNA
<213> ORGANISM: Artificial Sequence
<220> FEATURE:
<223> OTHER INFORMATION: Synthetic oligonucleotide: template miRNA3

<400> SEQUENCE: 12
ugauugagcc gcgccaauau c                                                     21

<210> SEQ ID NO 13
<211> LENGTH: 29
<212> TYPE: DNA
<213> ORGANISM: Artificial Sequence
<220> FEATURE:
<223> OTHER INFORMATION: Synthetic primer: RTp1

<400> SEQUENCE: 13
tgggctgacc tagaggtctt aacgtgctc                                             29

<210> SEQ ID NO 14
<211> LENGTH: 29
<212> TYPE: DNA
<213> ORGANISM: Artificial Sequence
<220> FEATURE:
<223> OTHER INFORMATION: Synthetic primer: RTp1

<400> SEQUENCE: 14
ccggaacaga caccaggttt aactagagc                                             29

<210> SEQ ID NO 15
<211> LENGTH: 29
<212> TYPE: DNA
<213> ORGANISM: Artificial Sequence
<220> FEATURE:
<223> OTHER INFORMATION: Synthetic primer: RTp1

<400> SEQUENCE: 15
ataccgatga gtgtgctacc aacgatatt                                             29

<210> SEQ ID NO 16
<211> LENGTH: 27
<212> TYPE: DNA
<213> ORGANISM: Artificial Sequence
<220> FEATURE:
<223> OTHER INFORMATION: Synthetic oligonucleotide: tag sequence T1

<400> SEQUENCE: 16
tggcaacatt tttcactggg tttatag                                               27

<210> SEQ ID NO 17
```

```
<211> LENGTH: 27
<212> TYPE: DNA
<213> ORGANISM: Artificial Sequence
<220> FEATURE:
<223> OTHER INFORMATION: Synthetic oligonucleotide:  tag sequence T2

<400> SEQUENCE: 17
ggttagcttc caaccacgtg tagatca                                         27

<210> SEQ ID NO 18
<211> LENGTH: 47
<212> TYPE: DNA
<213> ORGANISM: Artificial Sequence
<220> FEATURE:
<223> OTHER INFORMATION: Synthetic primer:  T1-X-F1
<220> FEATURE:
<221> NAME/KEY: misc_feature
<222> LOCATION: (27)..(28)
<223> OTHER INFORMATION: g at position 27 is joined to t at position 28
      by the azobenzene represented by Formula (5) of the specification.

<400> SEQUENCE: 18
tggcaacatt tttcactggg tttatagtgg gctgacctag aggtctt                  47

<210> SEQ ID NO 19
<211> LENGTH: 48
<212> TYPE: DNA
<213> ORGANISM: Artificial Sequence
<220> FEATURE:
<223> OTHER INFORMATION: Synthetic primer:  T1-X-R1
<220> FEATURE:
<221> NAME/KEY: misc_feature
<222> LOCATION: (27)..(28)
<223> OTHER INFORMATION: a at position 27 is joined to g at position 28
      by the azobenzene represented by Formula (5) of the specification.

<400> SEQUENCE: 19
ggttagcttc caaccacgtg tagatcagcg gcggtgacag aagagagt                 48

<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide:  tag sequence T3

<400> SEQUENCE: 20
cgcattgagc aagtgtacag agcat                                          25

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide:  tag sequencezT4

<400> SEQUENCE: 21
attatgcgtg gagaagcata tcata                                          25

<210> SEQ ID NO 22
<211> LENGTH: 45
<212> TYPE: DNA
<213> ORGANISM: Artificial Sequence
<220> FEATURE:
<223> OTHER INFORMATION: Synthetic primer:  T3-X-F3
<220> FEATURE:
<221> NAME/KEY: misc_feature
<222> LOCATION: (25)..(26)
<223> OTHER INFORMATION: t at position 25 is joined to c at position 26
``` by the azobenzene represented by Formula (5) of the specification.

<400> SEQUENCE: 22
cgcattgagc aagtgtacag agcatccgga acagacacca ggttt                45

<210> SEQ ID NO 23
<211> LENGTH: 46
<212> TYPE: DNA
<213> ORGANISM: Artificial Sequence
<220> FEATURE:
<223> OTHER INFORMATION: Synthetic primer:  T4-X-R4
<220> FEATURE:
<221> NAME/KEY: misc_feature
<222> LOCATION: (25)..(26)
<223> OTHER INFORMATION: a at position 25 is joined to c at position 26
      by the azobenzene represented by Formula (5) of the specification.

<400> SEQUENCE: 23
attatgcgtg gagaagcata tcatacggcg gtttggattg aaggga               46

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide:  tag sequence T5

<400> SEQUENCE: 24
aattgcgcat gtccatgtgt aa                                         22

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide:  tag sequenceT6

<400> SEQUENCE: 25
tactttagag gaaactgctg ag                                         22

<210> SEQ ID NO 26
<211> LENGTH: 42
<212> TYPE: DNA
<213> ORGANISM: Artificial Sequence
<220> FEATURE:
<223> OTHER INFORMATION: Synthetic primer:  T3-X-F3
<220> FEATURE:
<221> NAME/KEY: misc_feature
<222> LOCATION: (22)..(23)
<223> OTHER INFORMATION: a at position 22 is joined to a at position 23
      by the azobenzene represented by Formula (5) of the specification.

<400> SEQUENCE: 26
aattgcgcat gtccatgtgt aaataccgat gagtgtgcta cc                   42

<210> SEQ ID NO 27
<211> LENGTH: 42
<212> TYPE: DNA
<213> ORGANISM: Artificial Sequence
<220> FEATURE:
<223> OTHER INFORMATION: Synthetic primer:  T3-X-R3
<220> FEATURE:
<221> NAME/KEY: misc_feature
<222> LOCATION: (22)..(23)
<223> OTHER INFORMATION: g at position 22 is joined to t at position 23
      by the azobenzene represented by Formula (5) of the specification.

<400> SEQUENCE: 27

```
tactttagag gaaactgctg agttccttga ttgagccgcg cc                    42
```

```
<210> SEQ ID NO 28
<211> LENGTH: 27
<212> TYPE: DNA
<213> ORGANISM: Artificial Sequence
<220> FEATURE:
<223> OTHER INFORMATION: Synthetic oligonucleotide: probe 3
<220> FEATURE:
<221> NAME/KEY: modified_base
<222> LOCATION: (27)..(27)
<223> OTHER INFORMATION: modified with amino group.

<400> SEQUENCE: 28
ctataaaccc agtgaaaaat gttgcca                                    27

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide: probe 4
<220> FEATURE:
<221> NAME/KEY: modified_base
<222> LOCATION: (25)..(25)
<223> OTHER INFORMATION: modified with amino group.

<400> SEQUENCE: 29
ttgctctgta cacttgctca atgcg                                      25

<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide: probe 5
<220> FEATURE:
<221> NAME/KEY: modified_base
<222> LOCATION: (21)..(21)
<223> OTHER INFORMATION: modified with amino group.

<400> SEQUENCE: 30
ttacacatgg acatgcgcaa tt                                         22

<210> SEQ ID NO 31
<211> LENGTH: 27
<212> TYPE: DNA
<213> ORGANISM: Artificial Sequence
<220> FEATURE:
<223> OTHER INFORMATION: Synthetic oligonucleotide: probe 6
<220> FEATURE:
<221> NAME/KEY: modified_base
<222> LOCATION: (27)..(27)
<223> OTHER INFORMATION: modified with biotin.

<400> SEQUENCE: 31
gatcatacac gtggttggaa gctaacc                                    27

<210> SEQ ID NO 32
<211> LENGTH: 25
<212> TYPE: DNA
<213> ORGANISM: Artificial Sequence
<220> FEATURE:
<223> OTHER INFORMATION: Synthetic oligonucleotide: probe 7
<220> FEATURE:
<221> NAME/KEY: modified_base
<222> LOCATION: (24)..(24)
<223> OTHER INFORMATION: modified with biotin.

<400> SEQUENCE: 32
```

```
tatgatatgc ttctccacgc ataat                                          25
```

<210> SEQ ID NO 33
<211> LENGTH: 22
<212> TYPE: DNA
<213> ORGANISM: Artificial Sequence
<220> FEATURE:
<223> OTHER INFORMATION: Synthetic oligonucleotide: probe 8
<220> FEATURE:
<221> NAME/KEY: modified_base
<222> LOCATION: (22)..(22)
<223> OTHER INFORMATION: modified with biotin.

<400> SEQUENCE: 33

```
ctcagcagtt tcctctaaag ta                                             22
```

<210> SEQ ID NO 34
<211> LENGTH: 20
<212> TYPE: RNA
<213> ORGANISM: Artificial Sequence
<220> FEATURE:
<223> OTHER INFORMATION: Synthetic oligonucleotide: template miRNA1

<400> SEQUENCE: 34

```
ugacagaaga gagugagcac                                                20
```

<210> SEQ ID NO 35
<211> LENGTH: 21
<212> TYPE: RNA
<213> ORGANISM: Artificial Sequence
<220> FEATURE:
<223> OTHER INFORMATION: Synthetic oligonucleotide: template miRNA2

<400> SEQUENCE: 35

```
uuuggauuga agggagcucu a                                              21
```

<210> SEQ ID NO 36
<211> LENGTH: 21
<212> TYPE: RNA
<213> ORGANISM: Artificial Sequence
<220> FEATURE:
<223> OTHER INFORMATION: Synthetic oligonucleotide: template miRNA3

<400> SEQUENCE: 36

```
ugauugagcc gcgccaauau c                                              21
```

<210> SEQ ID NO 37
<211> LENGTH: 61
<212> TYPE: DNA
<213> ORGANISM: Artificial Sequence
<220> FEATURE:
<223> OTHER INFORMATION: Synthetic primer: RTp-T
<220> FEATURE:
<221> NAME/KEY: misc_feature
<222> LOCATION: (61)..(61)
<223> OTHER INFORMATION: n is a, c, g, or t

<400> SEQUENCE: 37

```
gttggctctg gtgcagggtc cgaggtattc gcaccagagc caactttttt tttttttttv    60
n                                                                    61
```

<210> SEQ ID NO 38
<211> LENGTH: 21
<212> TYPE: DNA
<213> ORGANISM: Artificial Sequence
<220> FEATURE:

```
<223> OTHER INFORMATION: Synthetic primer: B-F
<220> FEATURE:
<221> NAME/KEY: misc_feature
<222> LOCATION: (1)..(1)
<223> OTHER INFORMATION: modified with biotin.

<400> SEQUENCE: 38
tctggtgcag ggtccgaggt a                                              21

<210> SEQ ID NO 39
<211> LENGTH: 27
<212> TYPE: DNA
<213> ORGANISM: Artificial Sequence
<220> FEATURE:
<223> OTHER INFORMATION: Synthetic oligonucleotide: tag sequence T7

<400> SEQUENCE: 39
ggttagcttc caaccacgtg tagatca                                        27

<210> SEQ ID NO 40
<211> LENGTH: 48
<212> TYPE: DNA
<213> ORGANISM: Artificial Sequence
<220> FEATURE:
<223> OTHER INFORMATION: Synthetic primer: T1-X-R1
<220> FEATURE:
<221> NAME/KEY: misc_feature
<222> LOCATION: (27)..(28)
<223> OTHER INFORMATION: a at position 27 is joined to g at position 28
      by the azobenzene represented by Formula (5) of the specification.

<400> SEQUENCE: 40
ggttagcttc caaccacgtg tagatcagcg gcggtgacag aagagagt                 48

<210> SEQ ID NO 41
<211> LENGTH: 25
<212> TYPE: DNA
<213> ORGANISM: Artificial Sequence
<220> FEATURE:
<223> OTHER INFORMATION: Synthetic oligonucleotide: tag sequence T8

<400> SEQUENCE: 41
attatgcgtg gagaagcata tcata                                          25

<210> SEQ ID NO 42
<211> LENGTH: 46
<212> TYPE: DNA
<213> ORGANISM: Artificial Sequence
<220> FEATURE:
<223> OTHER INFORMATION: Synthetic primer: T3-X-R3
<220> FEATURE:
<221> NAME/KEY: misc_feature
<222> LOCATION: (25)..(26)
<223> OTHER INFORMATION: a at position 25 is joined to c at position 26
      by the azobenzene represented by Formula (5) of the specification.

<400> SEQUENCE: 42
attatgcgtg gagaagcata tcatacggcg gtttggattg aaggga                   46

<210> SEQ ID NO 43
<211> LENGTH: 22
<212> TYPE: DNA
<213> ORGANISM: Artificial Sequence
<220> FEATURE:
<223> OTHER INFORMATION: Synthetic oligonucleotide: tag sequence T9

<400> SEQUENCE: 43
tactttagag gaaactgctg ag                                             22
```

```
<210> SEQ ID NO 44
<211> LENGTH: 42
<212> TYPE: DNA
<213> ORGANISM: Artificial Sequence
<220> FEATURE:
<223> OTHER INFORMATION: Synthetic primer: T3-X-R3
<220> FEATURE:
<221> NAME/KEY: misc_feature
<222> LOCATION: (22)..(23)
<223> OTHER INFORMATION: g at position 22 is joined to t at position 23
      by the azobenzene represented by Formula (5) of the specification.

<400> SEQUENCE: 44
tactttagag gaaactgctg agttccttga ttgagccgcg cc                          42

<210> SEQ ID NO 45
<211> LENGTH: 27
<212> TYPE: DNA
<213> ORGANISM: Artificial Sequence
<220> FEATURE:
<223> OTHER INFORMATION: Synthetic oligonucleotide: probe 9
<220> FEATURE:
<221> NAME/KEY: modified_base
<222> LOCATION: (27)..(27)
<223> OTHER INFORMATION: modified with biotin.

<400> SEQUENCE: 45
gatcatacac gtggttggaa gctaacc                                           27

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide: probe 10
<220> FEATURE:
<221> NAME/KEY: modified_base
<222> LOCATION: (24)..(24)
<223> OTHER INFORMATION: modified with biotin.

<400> SEQUENCE: 46
tatgatatgc ttctccacgc ataat                                             25

<210> SEQ ID NO 47
<211> LENGTH: 22
<212> TYPE: DNA
<213> ORGANISM: Artificial Sequence
<220> FEATURE:
<223> OTHER INFORMATION: Synthetic oligonucleotide: probe 11
<220> FEATURE:
<221> NAME/KEY: modified_base
<222> LOCATION: (22)..(22)
<223> OTHER INFORMATION: modified with biotin.

<400> SEQUENCE: 47
ctcagcagtt tcctctaaag ta                                                22

<210> SEQ ID NO 48
<211> LENGTH: 48
<212> TYPE: DNA
<213> ORGANISM: Artificial Sequence
<220> FEATURE:
<223> OTHER INFORMATION: Synthetic primer: T-Xr-R
<220> FEATURE:
<221> NAME/KEY: misc_feature
<222> LOCATION: (27)..(28)
<223> OTHER INFORMATION: c at position 27 is joined to g at position 28
      by the 3'-3' and 5'-5' binding represented by Formula (1) of the
      specification.
```

```
<400> SEQUENCE: 48
ggttagcttc caaccacgtg tatgatcgcg gcggtgacag aagagagt                48

<210> SEQ ID NO 49
<211> LENGTH: 16
<212> TYPE: DNA
<213> ORGANISM: Artificial Sequence
<220> FEATURE:
<223> OTHER INFORMATION: Synthetic primer:  D-F
<220> FEATURE:
<221> NAME/KEY: misc_feature
<222> LOCATION: (1)..(1)
<223> OTHER INFORMATION: modified with DIG.

<400> SEQUENCE: 49
gtgcagggtc cgaggt                                                  16

<210> SEQ ID NO 50
<211> LENGTH: 27
<212> TYPE: DNA
<213> ORGANISM: Artificial Sequence
<220> FEATURE:
<223> OTHER INFORMATION: Synthetic oligonucleotide:  probe 12
<220> FEATURE:
<221> NAME/KEY: misc_feature
<222> LOCATION: (27)..(27)
<223> OTHER INFORMATION: modified with biotin.

<400> SEQUENCE: 50
gatcatacac gtggttggaa gctaacc                                      27
```